US008876757B2

(12) United States Patent
Jacobson et al.

(10) Patent No.: US 8,876,757 B2
(45) Date of Patent: Nov. 4, 2014

(54) FLUID LEVEL DETECTION SYSTEM

(75) Inventors: Jon D. Jacobson, Irvine, CA (US); Kyle Lynn, Costa Mesa, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 0 days.

(21) Appl. No.: 12/617,472

(22) Filed: Nov. 12, 2009

(65) Prior Publication Data

US 2011/0112472 A1   May 12, 2011

(51) Int. Cl.
*A61M 31/00*   (2006.01)
*A61F 9/007*   (2006.01)
*A61M 1/00*   (2006.01)
*A61M 37/00*   (2006.01)
*A61M 35/00*   (2006.01)

(52) U.S. Cl.
CPC ........ *A61F 9/00736* (2013.01); *A61M 37/0092* (2013.01); *A61M 35/00* (2013.01)
USPC .............................................. 604/67; 604/30

(58) Field of Classification Search
CPC . A61M 1/0023; A61M 1/0029; A61M 5/168; A61M 5/1684; A61M 5/172; A61M 37/0092; A61M 35/00; A61F 9/00736
USPC .......... 604/65–67; 340/619; 250/577; 73/293
See application file for complete search history.

(56) References Cited

U.S. PATENT DOCUMENTS

| | | | |
|---|---|---|---|
| 1,848,024 A | 3/1932 | Owen | |
| 3,116,697 A | 1/1964 | Theodore | |
| 3,781,142 A | 12/1973 | Zweig | |
| 4,189,286 A | 2/1980 | Murry et al. | |
| 4,193,004 A | 3/1980 | Lobdell et al. | |
| 4,564,342 A | 1/1986 | Weber et al. | |
| 4,644,177 A * | 2/1987 | Barabino | 250/577 |
| 4,773,897 A * | 9/1988 | Scheller et al. | 604/34 |
| 4,920,336 A | 4/1990 | Meijer | |

(Continued)

FOREIGN PATENT DOCUMENTS

| | | |
|---|---|---|
| DE | 10039765 A1 | 2/2002 |
| DE | 10039765 A1 * | 2/2002 |

(Continued)

OTHER PUBLICATIONS

Machine Translation of DE10039765, Translation acquired on Jun. 2014.*

(Continued)

*Primary Examiner* — Quynh-Nhu H Vu
*Assistant Examiner* — Jenna Zhang
(74) *Attorney, Agent, or Firm* — Abbott Medical Optics Inc.

(57) ABSTRACT

A medical device fluid sensing system is provided. The system includes a transmitter array positioned in association with a fluid maintaining device, such as a reservoir in a cassette. Electrical circuitry is connected to the transmitter array and configured to cause the transmitter array to transmit light energy at a predetermined wavelength and producing a desired absorption coefficient based on expected conditions within the fluid maintaining device. The system also includes a receiver array configured to receive light energy transmitted through the fluid maintaining device and originating from the transmitter array, and a controller configured to determine fluid level in the fluid maintaining device based on conditions sensed by the receiver array. In one embodiment, three transmitters and three matching sensors are provided in a surgical cassette, and when optical energy having predetermined characteristics is provided to the transmitter array, the presence or absence of fluid is determined.

21 Claims, 11 Drawing Sheets

(56) References Cited

U.S. PATENT DOCUMENTS

| | | | |
|---|---|---|---|
| 4,983,901 A | 1/1991 | Lehmer | |
| 5,006,110 A | 4/1991 | Garrison et al. | |
| 5,125,891 A | 6/1992 | Hossain et al. | |
| 5,195,960 A | 3/1993 | Hossain et al. | |
| 5,195,961 A | 3/1993 | Takahashi et al. | |
| 5,195,971 A | 3/1993 | Sirhan | |
| 5,230,614 A | 7/1993 | Zanger et al. | |
| 5,235,179 A * | 8/1993 | Chang et al. | 250/227.21 |
| 5,268,624 A | 12/1993 | Zanger | |
| 5,282,787 A | 2/1994 | Wortrich | |
| 5,342,293 A | 8/1994 | Zanger | |
| 5,454,783 A | 10/1995 | Grieshaber et al. | |
| 5,470,211 A | 11/1995 | Knott et al. | |
| 5,520,652 A | 5/1996 | Peterson | |
| 5,549,461 A | 8/1996 | Newland | |
| 5,591,127 A | 1/1997 | Barwick, Jr. et al. | |
| 5,657,000 A | 8/1997 | Ellingboe | |
| 5,676,530 A | 10/1997 | Nazarifar | |
| 5,676,650 A | 10/1997 | Grieshaber et al. | |
| 5,693,020 A | 12/1997 | Rauh | |
| 5,700,240 A | 12/1997 | Barwick, Jr. et al. | |
| 5,733,256 A | 3/1998 | Costin | |
| 5,747,824 A * | 5/1998 | Jung et al. | 250/577 |
| 5,830,176 A | 11/1998 | Mackool | |
| 5,899,674 A | 5/1999 | Jung et al. | |
| 5,928,257 A | 7/1999 | Kablik et al. | |
| 6,024,428 A | 2/2000 | Uchikata | |
| 6,062,829 A | 5/2000 | Ognier | |
| 6,086,598 A | 7/2000 | Appelbaum et al. | |
| 6,117,126 A | 9/2000 | Appelbaum et al. | |
| 6,150,623 A | 11/2000 | Chen | |
| 6,179,829 B1 | 1/2001 | Bisch et al. | |
| 6,260,434 B1 | 7/2001 | Holtorf | |
| 6,360,630 B2 | 3/2002 | Holtorf | |
| 6,436,072 B1 | 8/2002 | Kullas et al. | |
| 6,452,120 B1 | 9/2002 | Chen | |
| 6,452,123 B1 | 9/2002 | Chen | |
| 6,491,661 B1 | 12/2002 | Boukhny et al. | |
| 6,511,454 B1 | 1/2003 | Nakao et al. | |
| 6,632,214 B2 | 10/2003 | Morgan et al. | |
| 6,674,030 B2 | 1/2004 | Chen et al. | |
| 6,962,488 B2 | 11/2005 | Davis et al. | |
| 7,012,203 B2 | 3/2006 | Hanson et al. | |
| 7,070,578 B2 | 7/2006 | Leukanech et al. | |
| 7,169,123 B2 | 1/2007 | Kadziauskas et al. | |
| 7,244,240 B2 | 7/2007 | Nazarifar et al. | |
| 7,300,264 B2 | 11/2007 | Souza | |
| 2001/0051788 A1* | 12/2001 | Paukovits et al. | 604/67 |
| 2002/0019607 A1 | 2/2002 | Bui | |
| 2002/0036276 A1* | 3/2002 | Seeman | 250/573 |
| 2003/0073980 A1 | 4/2003 | Finlay et al. | |
| 2003/0108429 A1 | 6/2003 | Angelini et al. | |
| 2004/0037724 A1 | 2/2004 | Haser et al. | |
| 2005/0054971 A1 | 3/2005 | Steen et al. | |
| 2005/0069419 A1 | 3/2005 | Cull et al. | |
| 2005/0070859 A1 | 3/2005 | Cull et al. | |
| 2005/0118048 A1 | 6/2005 | Traxinger | |
| 2005/0245888 A1 | 11/2005 | Cull | |
| 2006/0145540 A1 | 7/2006 | Mezhinsky | |
| 2006/0219049 A1 | 10/2006 | Horvath et al. | |
| 2006/0219962 A1 | 10/2006 | Dancs et al. | |
| 2007/0016174 A1 | 1/2007 | Millman et al. | |
| 2007/0049898 A1 | 3/2007 | Hopkins et al. | |
| 2007/0287959 A1 | 12/2007 | Walter et al. | |
| 2008/0033342 A1 | 2/2008 | Staggs | |
| 2008/0066542 A1 | 3/2008 | Gao | |
| 2008/0112828 A1 | 5/2008 | Muri et al. | |
| 2008/0114289 A1 | 5/2008 | Muri et al. | |
| 2008/0114290 A1 | 5/2008 | King et al. | |
| 2008/0114291 A1 | 5/2008 | Muri et al. | |
| 2008/0114300 A1 | 5/2008 | Muri et al. | |
| 2008/0114301 A1 | 5/2008 | Bandhauer et al. | |
| 2008/0114311 A1 | 5/2008 | Muri et al. | |
| 2008/0114312 A1 | 5/2008 | Muri et al. | |
| 2008/0114372 A1 | 5/2008 | Edwards et al. | |
| 2008/0114387 A1 | 5/2008 | Hertweck et al. | |
| 2008/0125698 A1 | 5/2008 | Gerg et al. | |
| 2009/0013780 A1* | 1/2009 | Gao et al. | 73/293 |
| 2010/0134303 A1* | 6/2010 | Perkins | 340/619 |

FOREIGN PATENT DOCUMENTS

| | | |
|---|---|---|
| EP | 56019 A1 | 7/1982 |
| EP | 0777111 A1 | 6/1997 |
| EP | 1010437 A1 | 6/2000 |
| EP | 1310267 A2 | 5/2003 |
| EP | 1704839 A1 | 9/2006 |
| EP | 1787606 A1 | 5/2007 |
| EP | 1867349 A1 | 12/2007 |
| EP | 1873501 A1 | 1/2008 |
| EP | 1900347 A1 | 3/2008 |
| EP | 1935383 A1 | 6/2008 |
| GB | 2230301 A | 10/1990 |
| WO | 9317729 A1 | 9/1993 |
| WO | 9324082 A1 | 12/1993 |
| WO | 9632144 A1 | 10/1996 |
| WO | 9818507 A1 | 5/1998 |
| WO | 9917818 A1 | 4/1999 |
| WO | 0070225 A1 | 11/2000 |
| WO | 0234314 A1 | 5/2002 |
| WO | 2005084728 A2 | 9/2005 |
| WO | 2005092023 A2 | 10/2005 |
| WO | 2007143677 A2 | 12/2007 |
| WO | 2008060859 A1 | 5/2008 |
| WO | 2008060902 A1 | 5/2008 |

OTHER PUBLICATIONS

International Search Report for Application No. PCT/US2010/056436, mailed on Mar. 2, 2011, 4 pages.

Weber P., et al., "Optischer Sensor miBt Fullstande in Glasrohren," Feinwerktechnik & Messtechnik, 1991, vol. 99 (1 bar 2), pp. 31-33.

International Preliminary Report on Patentability and Written Opinion for Application No. PCT/US07/083875, mailed on May 12, 2009, 8 pages.

International Preliminary Report on Patentability and Written Opinion for Application No. PCT/US2010/056436, mailed on May 15, 2012, 7 pages.

International Search Report for Application No. PCT/US07/083875, mailed on May 7, 2008, 4 pages.

Phacoemulsification. Oct. 12, 2006. Wikipedia.com. Jun. 19, 2009 <http://en.wikipedia.org/wiki/Phacoemulsification>.

Water Structure and Science Article 6 pages http://www1.Isbu.ac.uk/water/vibrant.html, Updated Nov. 6, 2009 by Martin Chaplin.

* cited by examiner

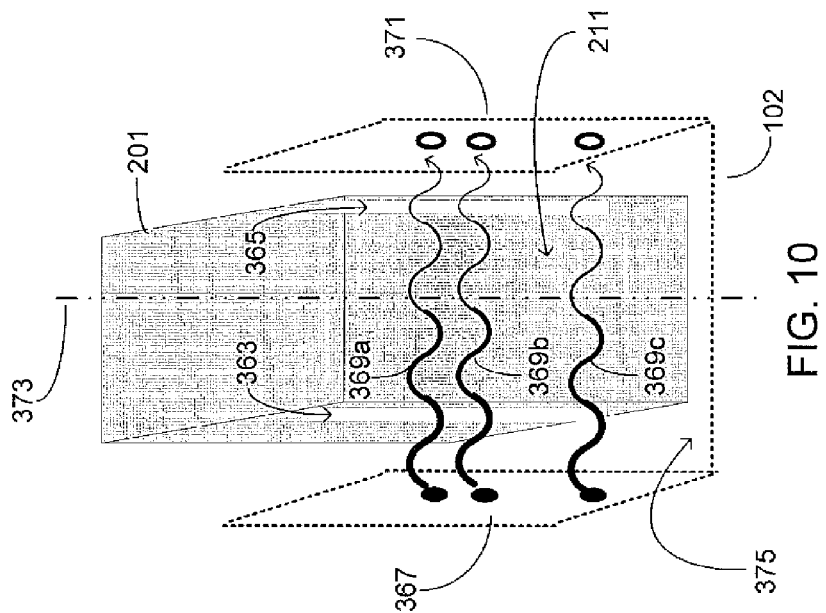
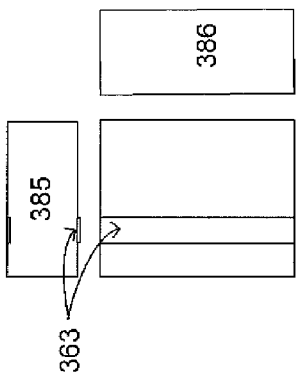
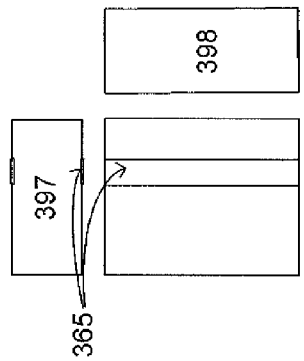
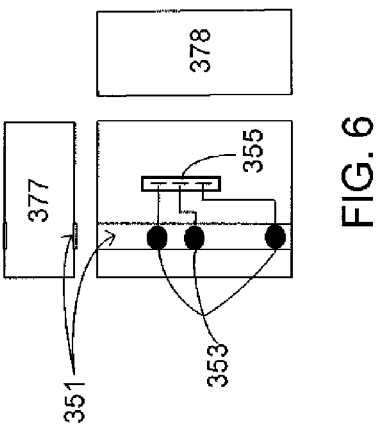
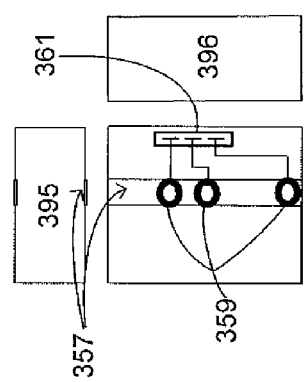

FLUID LEVEL DETECTION SYSTEM

BACKGROUND OF THE INVENTION

1. Field of the Invention

The present invention relates generally to the field of ocular surgery and more specifically, to managing fluid levels within a fluid container during surgical procedures, including ophthalmic procedures such as removal of a cataract.

2. Description of the Related Art

Phacoemulsification surgery has been successfully employed in the treatment of certain ocular problems, such as cataract surgery, including removal of a cataract-damaged lens and implanting an artificial intraocular lens. Phacoemulsification surgery typically involves removal of the cataract-damaged lens and may utilize a small incision at the edge of the patient's cornea. Through the small incision, the surgeon then creates an opening in the capsule, i.e. membrane that encapsulates the lens.

The surgeon may then insert an ultrasonic probe, incorporated within the phacoemulsification handpiece, through the opening in the cornea and capsule accessing the damaged lens. The handpiece's ultrasonic actuated tip emulsifies the damaged lens sufficient to be evacuated by the handpiece. After the damaged natural lens is completely removed, the handpiece tip is withdrawn from the patient. The surgeon may now implant an intraocular lens into the space made available in the capsule.

While performing phacoemulsification surgical techniques, such as lens removal, the surgeon may control a pump, such as a vacuum based pump (e.g. venturi), or a flow based pump (e.g. peristaltic pump), to pull fluids from the eye and through the handpiece tip. The pump is configured with a tank or reservoir positioned to hold the fluid until the tank fills to a certain point or level. During emulsification of the damaged lens, the tip of the phaco handpiece may collect fluids from the patient's eye and transfer the fluids for holding or temporarily storing in the surgical cassette reservoir. As the tip further collects fluid and material, the reservoir may fill with fluid to a point where the ratio of the volume of air with respect to the volume of fluid in the reservoir is outside of a desirable operating range. Typically, the desired operating range may dictate a minimum volume required for venting and reflux, a maximum volume to prevent the pump from exposure to fluids or from working into an uncompressible volume, and an intermediate or target volume representing a desired air-to-fluid ratio. During an ocular procedure, the air-to-fluid ratio may reach a point where the reservoir requires "rebalancing," which involves adding fluid to, or removing fluid from, the reservoir for the purpose of maintaining the desired operational ratio.

During the surgery it may become necessary for the surgeon to be able to remove fluid from a surgical cassette reservoir, or tank, into a waste or collection bag for the purpose of rebalancing the reservoir. One method for rebalancing the reservoir, when the fluid level exceeds the desirable operating range, involves the outflow of fluid and materials from the reservoir into the collection bag using a pump. When the fluid reaches a certain level the pump is turned on and removes or drains the reservoir. Alternatively, if the fluid level in the reservoir falls below a low level threshold, rebalancing may involve the inflow of fluid from an infusion bottle into the reservoir. In either arrangement, when the reservoir air-to-fluid ratio is returned within desirable operating values, indicating the reservoir is 'balanced,' the pump is stopped which in turn stops the flow of fluid and materials.

Maintaining a proper air-to-fluid ratio or balance within the reservoir may allow the surgeon to perform various aspiration, vacuum venting, and reflux surgical procedures without interruption. When the reservoir level reaches an upper level threshold, thus requiring outflow or removal of fluid, the instrument host typically turns on a pump to move the fluid from the reservoir to the collection bag.

In order to remove fluid, current designs typically determine the proper time to activate a peristaltic reservoir pump by sensing the fluid level in the reservoir. Today's designs typically involve the use of a float mechanism, an optical or sound emitter-sensor system, or the capacitance of a circuit involving the fluid. For example, current optical system implementations typically involve designs measuring the amount of reflected or refracted energy received at one or more photo-detection sensors from a linear light source as light travels through the air and fluid within the reservoir.

While certain detection sensor devices have previously been offered, reliability in air-fluid reservoir balancing in these cassettes can at times be imperfect, particularly in precise operating environments. Some previous designs include a float mechanism, which can fail by sticking to the side of the reservoir, or the float may "sink" into the reservoir. Optical and sound mechanisms tend to be costly to deploy, and in certain cases are unreliable when the sensing path is subjected to condensation, droplets, debris, or foam.

It would be beneficial to offer a surgical cassette that employs minimal components or components that efficiently control and maintain the fluid level within the cassette reservoir as required in surgical environments, including but not limited to the ocular surgical environment.

SUMMARY OF THE INVENTION

According to one aspect of the present design, there is provided a medical device fluid sensing system. The system includes a transmitter positioned in association with a fluid maintaining device, such as a reservoir in a cassette. Electrical circuitry is connected to the transmitter and configured to cause the transmitter to transmit light energy at a predetermined wavelength and produce a desired absorption coefficient based on expected conditions within the fluid maintaining device. The system also includes a receiver configured to receive light energy transmitted through the fluid maintaining device and originating from the transmitter, and a controller configured to determine fluid level in the fluid maintaining device based on conditions sensed by the receiver. In one embodiment, three transmitters and three matching sensors are provided in a surgical cassette, and when optical energy having predetermined characteristics is provided to the transmitter, the presence or absence of fluid is determined.

These and other advantages of the present invention will become apparent to those skilled in the art from the following detailed description of the invention and the accompanying drawings.

BRIEF DESCRIPTION OF THE DRAWINGS

The present invention is illustrated by way of example, and not by way of limitation, in the figures of the accompanying drawings in which:

FIG. 6 shows a top, side, and front view of the left side of the cassette with integral light sources in accordance with an aspect of the present design;

FIG. 7 shows a top, side, and front view of the right side of the cassette with integral light sensors in accordance with another aspect of the present design;

FIG. 8 shows a top, side, and front view of the left side of the cassette with an integrated window in accordance with a further aspect of the present design;

FIG. 9 shows a top, side, and front view of the right side of the cassette with an integrated window in accordance with a further aspect of the present design;

FIG. 10 shows a centerline split perspective view illustrating a combined left and right side views for the cassette loaded into a holder in accordance with another aspect of the present design;

DETAILED DESCRIPTION OF THE DESIGN

Figure 1:
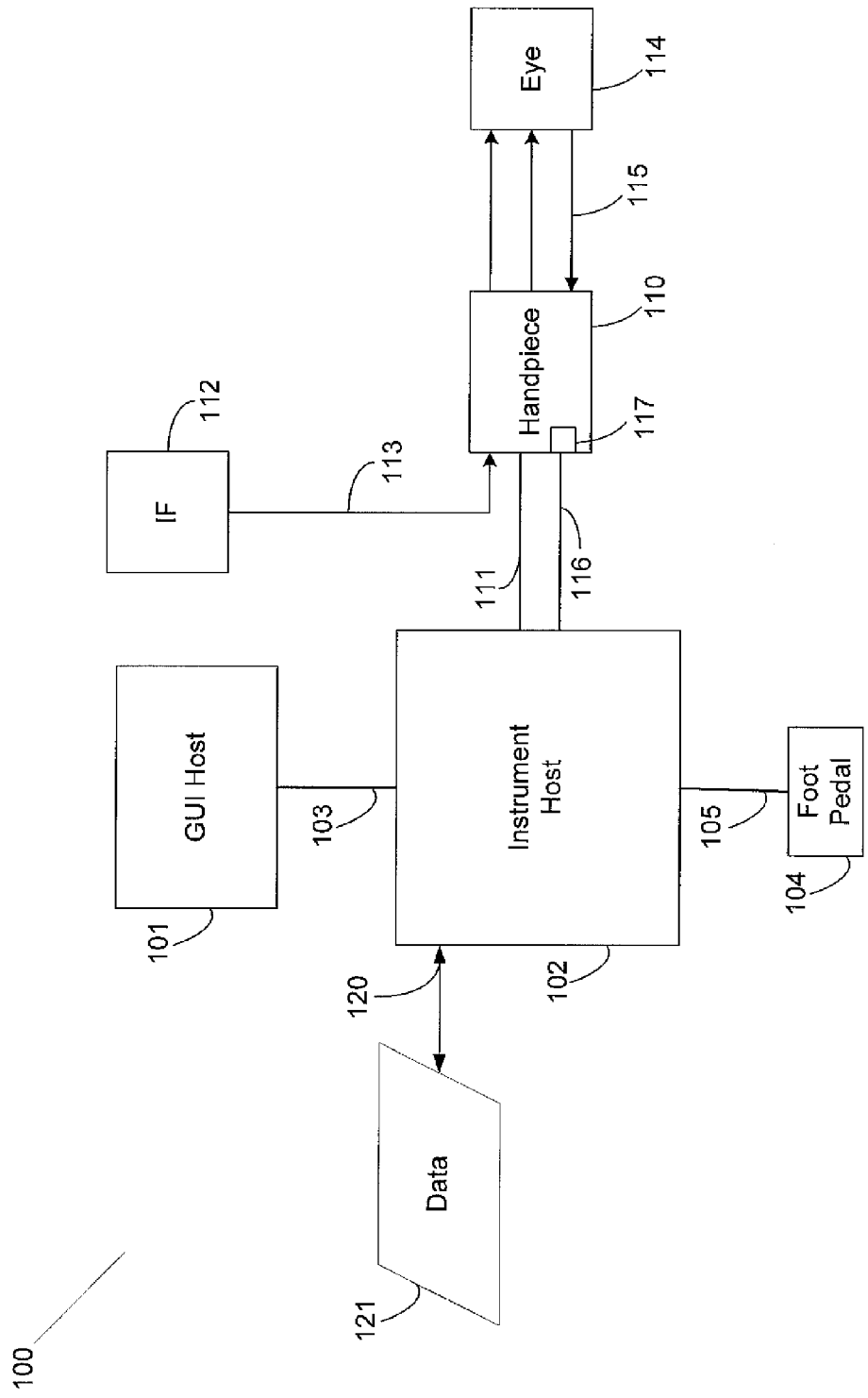
FIG. 1 illustrates an exemplary phacoemulsification/vitrectomy system in a functional block diagram.

The following description and the drawings illustrate specific embodiments sufficient to enable those skilled in the art to practice the system and method described. Other embodiments may incorporate structural, logical, process and other changes. Examples merely typify possible variations. Individual components and functions are generally optional unless explicitly required, and the sequence of operations may vary. Portions and features of some embodiments may be included in or substituted for those of others.

The present design is directed to determining fluid level, such as detecting the fluid level within a surgical cassette's integrated air-fluid reservoir and mechanized controlling of the fluid level within the reservoir. The present arrangement may include a device, such as a pump (peristaltic, venturi, etc.), configured to provide outflow/inflow of fluid from the air-fluid reservoir and move the fluid to a collector such as a collection bag or from a fluid source such as a BSS bottle for purposes of maintaining proper balance of air and fluid in the reservoir.

The present design employs one or more light illumination and light detection device pairs, where the illumination and detection device pairs may operate as optical wavelength emitting and detecting device pairs configured with the air-fluid reservoir within the surgical cassette system. The optical wavelength and absorption coefficient for the light energy transmitted through the reservoir are predetermined based on expected conditions within the reservoir. The present design may arrange the emitting and detecting device pairs to detect the level of fluid within the cassette's reservoir where the device pairs are connected to an electric circuit configured to control the fluid level within the reservoir.

For example, the phacoemulsification system may provide for vacuum regulated aspiration, where a surgeon performing an ocular surgical procedure may remove a relatively large volume of fluid and material from the patient's eye. Vacuum regulated aspiration may increase the fluid level within the surgical cassette's reservoir in a short amount of time. If the reservoir receives too much fluid, the level may rise above an acceptable level and may inhibit performance. For example, a rise in fluid level above certain reservoir fluid connections may cause the phacoemulsification system to operate improperly or stop altogether.

During vacuum regulated aspiration, the phacoemulsification system moves fluid from the eye to a reservoir. In order to remove fluid from the reservoir, the phaco system may operate a pump configured to move the fluid from the reservoir and into a collection bag. The present design's optical fluid level detection system may include an electric circuit configured to determine the light energy received from at least one detection device where the light energy is measured at at least one distinct vertical height within the reservoir. In one embodiment, three such detection devices are employed at three distinct heights within the reservoir, but any number of pairs may be employed. As the fluid level within the reservoir rises, the light energy received by at least one optical wavelength detector will decrease when submerged in the fluid, due to absorption of light energy by the fluid and ocular material present. Such a decrease in light energy received results in an attenuation of the transmitted signals, where the electric circuit configuration senses the decrease in light energy received. Conversely, as the fluid level decreases inside the reservoir, the electric circuit may detect an increase in light energy received by at least one optical wavelength detector as determined by the electric circuit. In this arrangement, the present design may produce control signals to start and stop a pump situated between the reservoir and collection bag based on the amount of light energy detected at predetermined vertical heights within the reservoir.

The system can operate the pump to add or remove fluid from the reservoir when the level falls outside of preset thresholds, either upper or lower, and stop the pump when the level is restored within the desired operational range. A surgeon performing an ocular surgical procedure may input the desired thresholds via the instrument host system or GUI host prior to surgery, or the desired thresholds may be preset by the manufacturer. In this way, the present design may allow the surgeon to focus on the ocular procedure without the need to monitor and manually adjust the air-to-fluid ratio or balance within the reservoir.

The present design thus comprises a fluid level detecting and controlling arrangement that may be used with a medical instrument system, such as a phacoemulsification system. The system can be provided with a reservoir in a surgical cassette system together with a pump to control the flow of fluid from the reservoir. Newer cassettes can support aspiration and infusion functionality, enabling the surgeon to control the operation of the phacoemulsification/vitrectomy system handpiece.

The present design is intended to provide reliable, noninvasive, and efficient fluid level detecting and control in a medical instrument system for use in efficiently managing and maintaining the air-fluid balance by controlling the flow of fluids during an ocular procedure.

System Example

While the present design may be used in various environments and applications, it will be discussed herein with a particular emphasis on an environment where a surgeon or health care practitioner performs. For example, one embodiment of the present design is in or with a phacoemulsification surgical system that comprises an independent graphical user interface (GUI) host module, an instrument host module, a GUI device, and a controller module, such as a foot switch, to control the surgical system.

FIG. 1 illustrates an exemplary phacoemulsification/vitrectomy system 100 in a functional block diagram to show the components and interfaces for a safety critical medical instrument system that may be employed in accordance with an aspect of the present invention. A serial communication cable 103 connects GUI host 101 and instrument host 102 for the purposes of controlling the surgical instrument host by the GUI host. Instrument host 102 may be considered a computational device in the arrangement shown, but other arrangements are possible.

An interface communications cable 120 is connected to instrument host 102 for collecting data 121, such as sensor data, settings, and parameter information. Instrument host 102 may distribute instrument settings and parameters information to other systems, subsystems and modules within and external to instrument host 102. Although shown connected to the instrument host 102, interface communications cable 120 may be connected or realized on any other subsystem (not shown) that could accommodate such an interface device able to collect and distribute the respective data.

A switch module associated with foot pedal 104 may transmit control signals relating internal physical and virtual switch position information as input to the instrument host 102 over serial communications cable 105. While not shown in the present drawing, any mode of communication may be employed, including but not limited to wired communication as shown or wireless communication. Instrument host 102 may provide a database file system for storing configuration parameter values, programs, and other data saved in a storage device (not shown), such as upper and lower fluid level preset thresholds ensuring that a 'balanced' condition, or proper air-to-fluid ratio, is maintained within the reservoir. In addition, the database file system may be realized on GUI host 101 or any other subsystem (not shown) that could accommodate such a file system.

The phacoemulsification/vitrectomy system 100 has a handpiece 110 that includes a needle and electrical means, typically a piezoelectric crystal, for ultrasonically vibrating the needle. The instrument host 102 supplies power on line 111 to phacoemulsification/vitrectomy handpiece 110. An irrigation fluid source 112 can be fluidly coupled to handpiece 110 through line 113. The irrigation fluid and ultrasonic power are applied by handpiece 110 to a patient's eye, or affected area or region, indicated diagrammatically by block 114. Alternatively, the irrigation source may be routed to eye 114 through a separate pathway independent of the handpiece. Aspiration is provided from eye 114 by a pump (not shown), such as a peristaltic pump, via the instrument host 102, through lines 115 and 116. Optionally, a switch 117 disposed on handpiece 110 may be utilized to enable a surgeon/operator to select an amplitude of electrical pulses to the handpiece via the instrument host and the GUI host. Any suitable input device, such as for example, foot pedal 104 may be utilized in lieu of switch 117.

In combination with phacoemulsification system 100, the present system enables aspiration or infusion functionality in or with the phacoemulsification system and may comprise components including, but not limited to, a selector valve (which may be one or more valves, including but not limited to a pinch valve), one or more peristaltic pumps, reservoir, vacuum regulator, and collection bag.

The fluid level detection employed is described with respect to a phacoemulsification system having dual pump capability and employing a reservoir, such as the WHITESTAR Signature system available from Abbott Medical Optics Inc. (AMO), of Santa Ana, Calif. Although the present discussion references operational features and functionality in context with systems such as the AMO WHITESTAR Signature System, the present design is not limited to designs involving dual pump capability or a replaceable cassette and may apply to virtually any fluid based medical design where accurate fluid level detection and control is desirable.

Figure 2A:
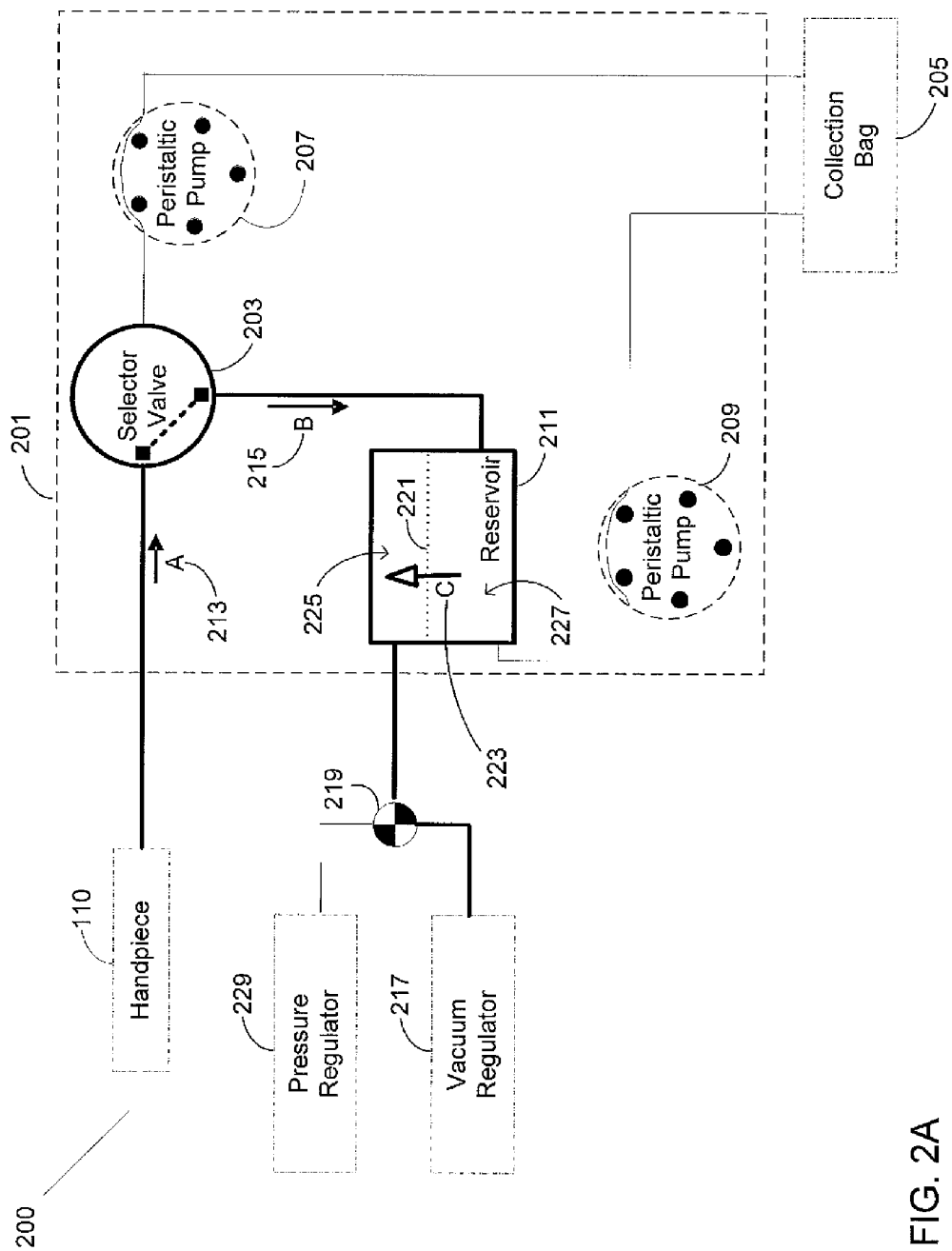
FIG. 2A illustrates an exemplary surgical system in a functional block diagram that shows the vacuum regulated aspiration components and interfaces.
Figure 2B:
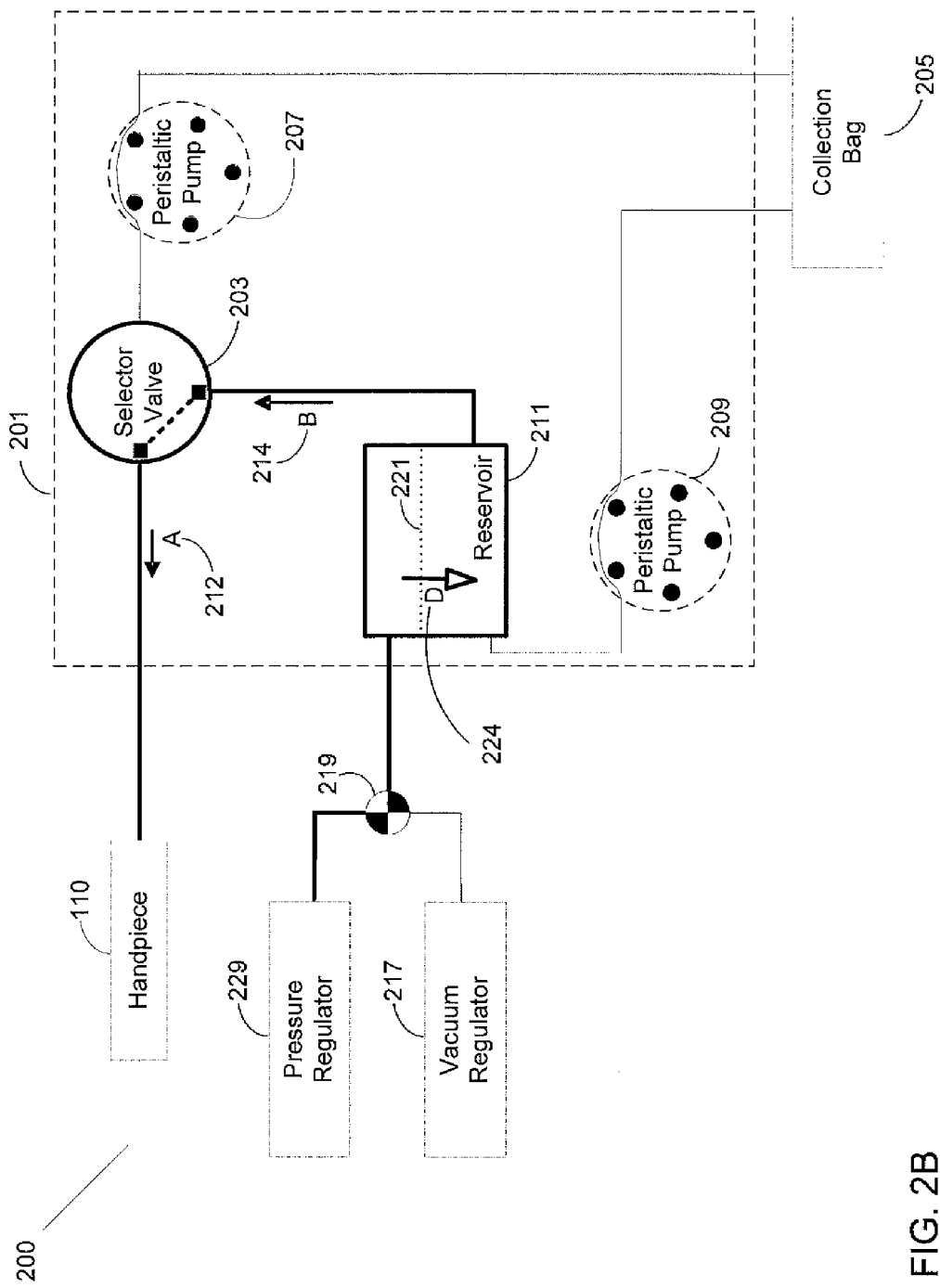
FIG. 2B illustrates an exemplary surgical system in a functional block diagram that shows the pressure regulated infusion components and interfaces.

FIG. 2A illustrates an exemplary surgical system in a functional block diagram that shows the vacuum regulated aspiration components and interfaces that may be employed in accordance with an aspect of the present design. FIG. 2B illustrates the exemplary surgical system including components and interfaces for pressure regulated infusion functions. The present design effectively connects the aspiration line from the handpiece to the air-fluid reservoir, and the reservoir is also connected to the collection bag through a peristaltic line. The peristaltic connection between the reservoir and collection bag involves a peristaltic pump operating clockwise for outflow of fluid from the reservoir to the collection bag.

Surgical system 200 may include a selector valve, peristaltic aspiration pump, reservoir, vacuum regulated aspiration, peristaltic reservoir pump, collection bag, and interconnecting surgical tubing as shown in FIGS. 2A and 2B. Cassette 201 may include connections to facilitate easy attachment to and removal from the instrument host as well as handpiece 110, valve 203 and collection bag 205. The present design contemplates two pumps for aspiration as shown in FIGS. 2A and 2B, where the surgical cassette may operate with surgical tubing or other appropriate interconnections interfacing with the two pumps. Surgical system 200 may provide for peristaltic aspiration and reflux functionality by operating peristaltic pump 207 illustrated in FIGS. 2A and 2B.

Cassette 201 is illustrated in FIGS. 2A and 2B to show components that may be enclosed within the cassette. The size and shape of cassette 201 is not to scale, and note that certain components, notably peristaltic aspiration pump 207 and peristaltic reservoir pump 209, interface with the cassette but in actuality form part of the medical device to which the cassette attaches. Further, more or fewer components may be included in cassette 201 than are shown in FIGS. 2A and 2B depending on the circumstances and implementation of the cassette.

Referring to FIG. 2A, handpiece 110 is connected to selector valve 203 in cassette 201 typically by surgical tubing. The present design may configure selector valve 203 to interface between handpiece 110 and reservoir 211. In this configuration, the system may operate selector valve 203 to connect handpiece 110 with reservoir 211 based on signals received from the instrument host resulting from the surgeon's input to the GUI host. In the arrangement where selector valve 203 connects handpiece 110 with reservoir 211, the present design may allow for vacuum regulated aspiration of fluid from the eye directly to reservoir 211 as indicated by the flow in the directions of arrow A 213 and arrow B 215 by operating vacuum regulator 217 through valve 219, for example a check valve. Vacuum regulated aspiration and reduction of air pressure may cause air-fluid interface 221 to move in an upward direction as illustrated in the direction of arrow C 223, thus the present design may aspirate fluid from the eye to the reservoir. Reservoir 211 may contain air in section 225 and fluid in section 227 separated by air-fluid interface 221, i.e. the boundary where air and fluid meet within the reservoir. The present design may involve valve 219 positioned to connect either vacuum regulator 217 or pressure regulator 229.

FIG. 2B illustrates the cassette system selector valve 203 that connects handpiece 110 with reservoir 211. The present design may provide infusion of fluid from reservoir 211 or the tubing between the reservoir and handpiece 110 directly to the eye as indicated by the directions of arrow A 212 and arrow B 214. As pressure regulator 229 increases the air pressure inside of reservoir 211, fluid is pushed out of reservoir 211 towards the eye via handpiece 110. This increase of pressure may cause air-fluid interface 221 to move in a downward direction as indicated by the direction of arrow D 224, thus the present design infuse fluid from reservoir 211 or the tubing between the reservoir and handpiece 110 to the eye.

Surgical cassette system 201 may connect reservoir 211 with collection bag 205 using surgical tubing. For simplicity, only the vacuum and pressure regulated operations are illustrated in FIGS. 2A and 2B. Peristaltic pump 207 may provide for aspiration and reflux functionality for the eye at handpiece 110 and is shown for completeness. In this arrangement, as peristaltic pump 207 operates in a clockwise direction, the present design moves fluid from the eye to collection bag 205 for aspiration. Counter-clockwise operation of pump 207 enables peristaltic reflux/infusion of the eye.

Peristaltic reservoir pump 209, a component within the instrument host, and the collector, collection bag 205, in combination may enable surgical system 200 to remove unwanted settled material from reservoir 211. The surgical tubing portion of surgical system 200 may include the fluid connections, for example flexible tubing, between each component represented with solid lines in FIGS. 2A and 2B.

Vacuum regulator 217, a component within the instrument host, may be connected with reservoir 211 through valve 219. In this arrangement, vacuum regulator 217 may operate to remove air from the top of reservoir 211 and deliver the air to atmosphere (not shown). Removal of air from the reservoir 211 in this manner may reduce the pressure within the reservoir, which reduces the pressure in the attached aspiration line, to a level less than the pressure within the eye. This lower pressure may cause fluid to move from the patient's eye, thereby providing aspiration. The present design vacuum regulator 217 and reservoir 211 arrangement may enable surgical system 200 to provide fluid to reservoir 211.

Pressure regulator 229, a component within the instrument host, may be connected with reservoir 211 through valve 219. Pressure regulator 229 may operate to provide pressurized air into the top of reservoir 211. Pushing air into reservoir 211, for example to a level greater than the pressure present in the eye, may increase the air pressure within reservoir 211. Increased air pressure may in turn reduce the amount of fluid by pushing the fluid out of reservoir 211 and toward handpiece 110. This higher pressure may cause fluid to move from reservoir 211 or the tubing between the reservoir and handpiece 110 to the patient's eye, thereby providing reflux/infusion. The present design pressure regulator 229 and reservoir 211 arrangement may enable surgical system 200 to provide fluid to the patient's eye.

Fluid Level Detection

Figure 12:
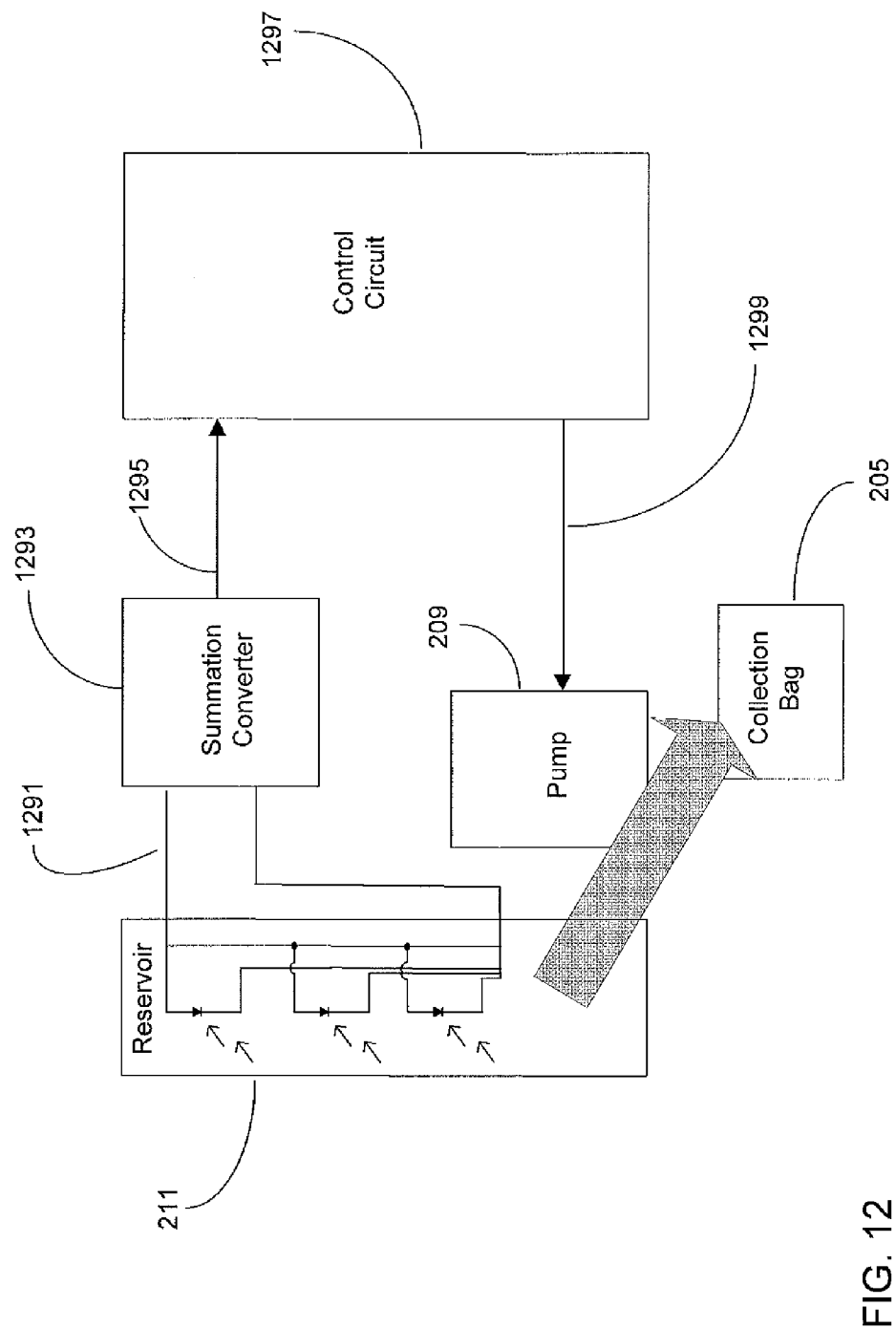
FIG. 12 illustrates an exemplary electric circuit.

The present design provides an alternative to sensing techniques using either a float mechanism, ultrasound emitter-sensor system, or the capacitance of a circuit involving the fluid. The present design includes a fluid level detection technique wherein optical emitter and detector devices are paired, typically involving photo-diodes, and may arrange each pair at different vertical height positions, forming multiple horizontally directed optical transmission paths through the reservoir. The optical emitter and detector device pairs may connect to an electric circuit configured to power and operate the emitters, i.e. light sources, and determine the light energy received by the detectors, i.e. light sensors, after following a transmission path through either air or fluid, e.g. water, balanced salt solution (BSS), or other suitable liquids and solutions, stored within the surgical cassette reservoir. The electric circuit may communicate the received or detected light energy as a signal to the phacoemulsification instrument host for purposes of determining the fluid level based on the amount of received light energy from each optical wavelength detector. In a further embodiment of the present design, the circuit may communicate the signal to a separate or self-contained control circuit 397, such as is shown in FIG. 12. Based on the level determined by the instrument host, a peristaltic reservoir pump may be operated to add or remove fluid from the reservoir.

According to Chaplin, M. F., "Water Structure and Science," last update 13 Dec. 2008 (article currently available at www.lsbu.ac.uk/water/vibrat.html), the absorption coefficient $\mu_{a(\lambda)}$ at a particular wavelength ($\lambda$) for liquid water realized between an optical emitter and detector, arranged in accordance with the present design, may be determined according to:

$$\frac{I}{I_0} = e^{-\mu_a(\lambda)x} \qquad (1)$$

where I is the intensity of the light after passing through the sample, $I_0$ is the intensity of the incident light and x is the path length in centimeters (cm).

Simply put, Equation (1) shows that the absorption coefficient is directly proportional to the intensity of the transmitted light and indirectly proportional to the incident intensity of the light.

Figure 3:
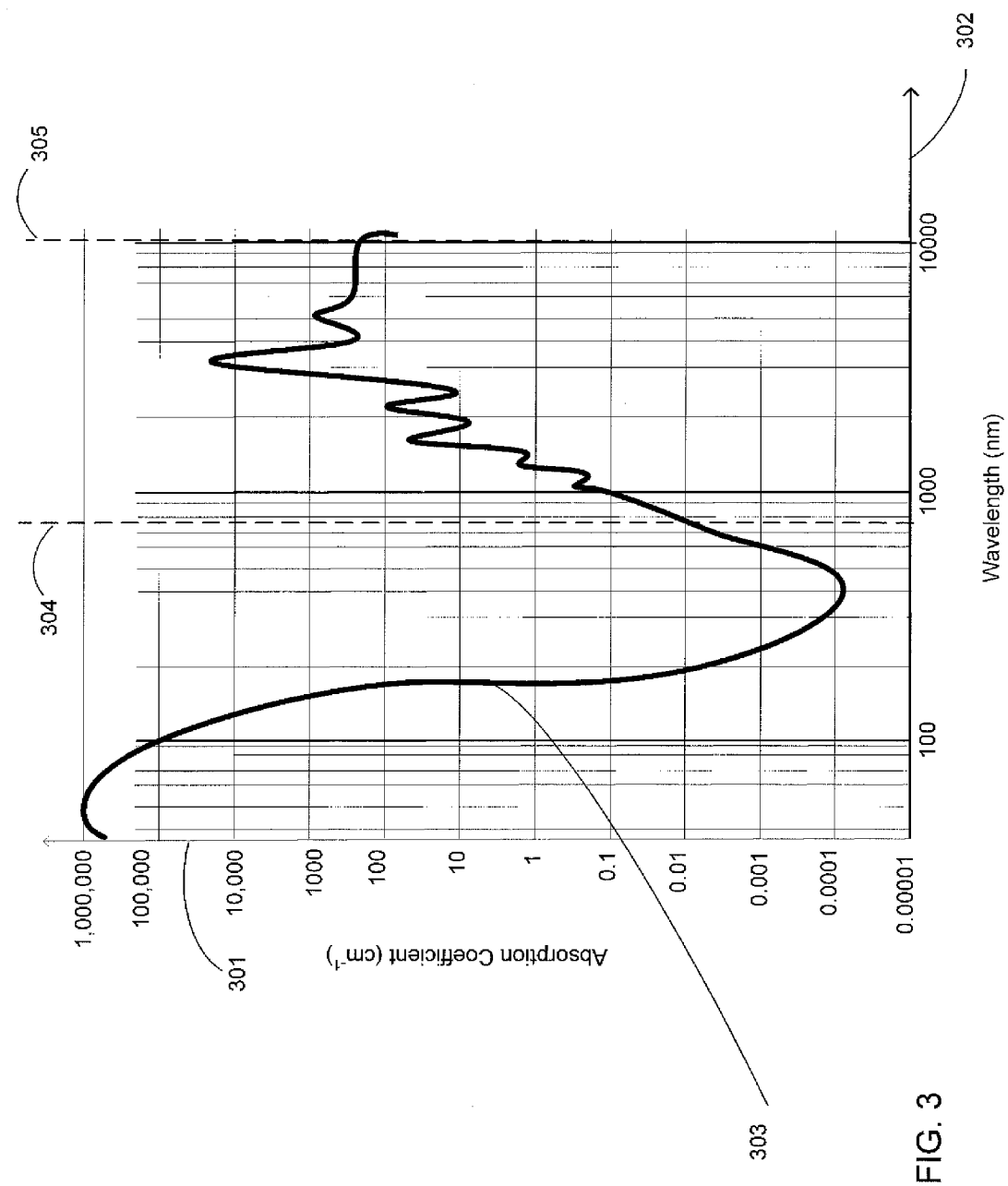
FIG. 3 illustrates a general approximation for a continuous curve showing the main features for the absorption coefficients for liquid water.

FIG. 3 is a general approximation for a continuous curve showing the main features for the absorption coefficients for liquid water resulting from Equation (1). The curve expresses the expected amount of optical energy that may be attenuated for various light wavelengths transmitted through water. The large difference in optical wavelength absorption between air and fluid, such as BSS, may allow the present design's optical fluid level detection system to determine the fluid level in the reservoir or a tank based on light intensity received at the sensing element in view of the expected light intensity to be absorbed and received. Ocular material held or suspended in the reservoir may increase the absorption of light energy, and as a result may further enable the present design to detect the absence or presence of fluid in the reservoir.

Simply put, light energy transmitted through air will yield a higher light intensity received at a receiver than light transmitted through fluid. Thus light energy absorbed by fluid and/or other material results in a lower reading of light energy, indicating fluid is blocking the sensor, or has reached the level of the sensor.

The absorbance (A, in optical density units) of light energy in liquid water is determined by:

$$A = -\text{Log}_{10}\left(\frac{I}{I_0}\right) \qquad (2)$$

The transmittance (T) of water is defined as shown in Equation (3).

$$T = \left(\frac{I}{I_0}\right) \qquad (3)$$

where the transmittance represents the relationship between the intensity of the light energy relative to the intensity of incident light that passes through the water at a given wavelength.

Transmittance may be related to absorbance as shown in Equation (4):

$$A = -\log_{10}\tau = -\log_{10}\left(\frac{I}{I_0}\right) \qquad (4)$$

where $\tau$ in Equation (4) represents transmittance. Transmittance is calculated according to Equation (5):

$$\tau = e^{-\alpha x} \qquad (5)$$

where $\alpha$ is the attenuation coefficient and x is the path length.

From the foregoing equations and other equations generally known to those skilled in the art, a range of acceptable expected light energy levels in air and water may be computed for light emitted at a particular wavelength. For example, at wavelength X, transmission of light over distance Y through air may result in a receiving sensor receiving light energy in a range between A and B, while transmission through water may result in received light energy in the range between P and Q, which is lower than A and B. A "dividing line" between the lowest light energy expected in air and the highest light energy expected in fluid may be determined, such that a reading below the dividing line indicates the presence of fluid while above the dividing line indicates the absence of fluid. Other measurements or algorithms may be employed.

Thus the present design may involve a computational algorithm configured to determine the absorption coefficient, transmittance, and/or absorbance coefficient sufficient for use in determining whether fluid is present in the optical transmission path through the reservoir, or only air, according to the foregoing equations and other equations known to those skilled in the art.

With respect to selection of an appropriate wavelength, referring to FIG. 3, absorption coefficient (on axis 301) is plotted against wavelength (on axis 302) to realize absorption coefficient curve 303 characterizing the absorption coefficients at various optical wavelengths. Absorption coefficient curve 303 may yield possible ranges for use with the present designs fluid level detection arrangement. A first usable range may be found at wavelengths in the ultraviolet (UV) range below approximately 110 nm, and a second useable range may be found at wavelengths in the infrared (IR) range at approximately 950 nm and higher.

As may be appreciated by a review of FIG. 3 and an understanding that certain water impurities may exist, the term "approximately" employed herein, such as "approximately 950 mm and higher" represents a general value relatively near the cited value wherein adequate performance has been observed. Without limitation, it is to be understood that "approximately" may refer, in the context of FIG. 3, to any value wherein the curve shown exhibits an absorption coefficient in excess of 0.0001 and a wavelength in excess of 500 nm, and in many cases in excess of 800 or 900 nm.

Currently, emitter and detector components operating in the IR range may provide for a more effective and efficient design when compared to the availability and cost of UV range components. In addition, absorption coefficient curve 303 exhibits a more gradual slope of the curve segment within the IR range when compared to the UV curve slope, where the gradual slope found in the IR range may provide further design flexibility with choosing emitter device optical power and electrical amplification and detection circuit devices. Based on device availability, cost, and performance, and the present design with a path length of 1 cm, the fluid level detection arrangement may operate at wavelengths from 750 nm or higher. In an embodiment, with a path length of 1 cm, the fluid level detection arrangement may operate at wavelengths between 750 nm to 10,000 nm as shown in FIG. 3, reference numbers 304 and 305. Using path length as the variable in Equations (1)-(5) above, a particular wavelength can be determined and implemented successfully. Based on the Equations (1)-(5) above we can take a particular wavelength and accommodate the other components to successfully implement that model. Alternative designs can be derived using wavelengths lower than 750 nm by utilizing an optical path longer than 1 cm.

Arranging one or more IR emitter-detector device pairs configured with the surgical cassette's reservoir may produce an electric signal output level that changes proportionally to the amount of fluid stored in the reservoir. The present design may involve a plurality of IR emitter-detector detection device pairs and may position these pairs at various predetermined vertical heights between the bottom and the top of the reservoir.

It is noted that the system may employ a single relatively long IR emitter-detector device pair. Use of such a pair would provide a gradient signal depending on the amount of the detector being covered by fluid.

An alternative configuration, not illustrated, uses an emitter-detector arrangement in a vertical configuration with one side, such as the emitter, positioned at the top of the reservoir and the other side, such as the detector, located on the bottom of the reservoir to measure the vertical height or "thickness" of the fluid.

As discussed, in the situation where the fluid level rises in the reservoir until the detector devices are submerged, the result is a decrease in the optical power output signal representing the optical or light energy received at each detector device. Conversely, as the fluid level within the reservoir falls, exposing the detector devices to air, the resulting optical power output signal produced from the optical energy received from each detector device typically increases. Thus continuously detecting the optical energy received from each of the present design's emitter-detector device pairs arranged with the reservoir may efficiently enable determining the reservoir fluid level.

In summary, the received optical power or light energy formed by the present design's detector devices is at a maximum when the reservoir is empty, i.e. full of air, and is at a minimum when the reservoir is full, i.e. full of fluid such as water, BSS, and/or ocular material.

Figure 4:
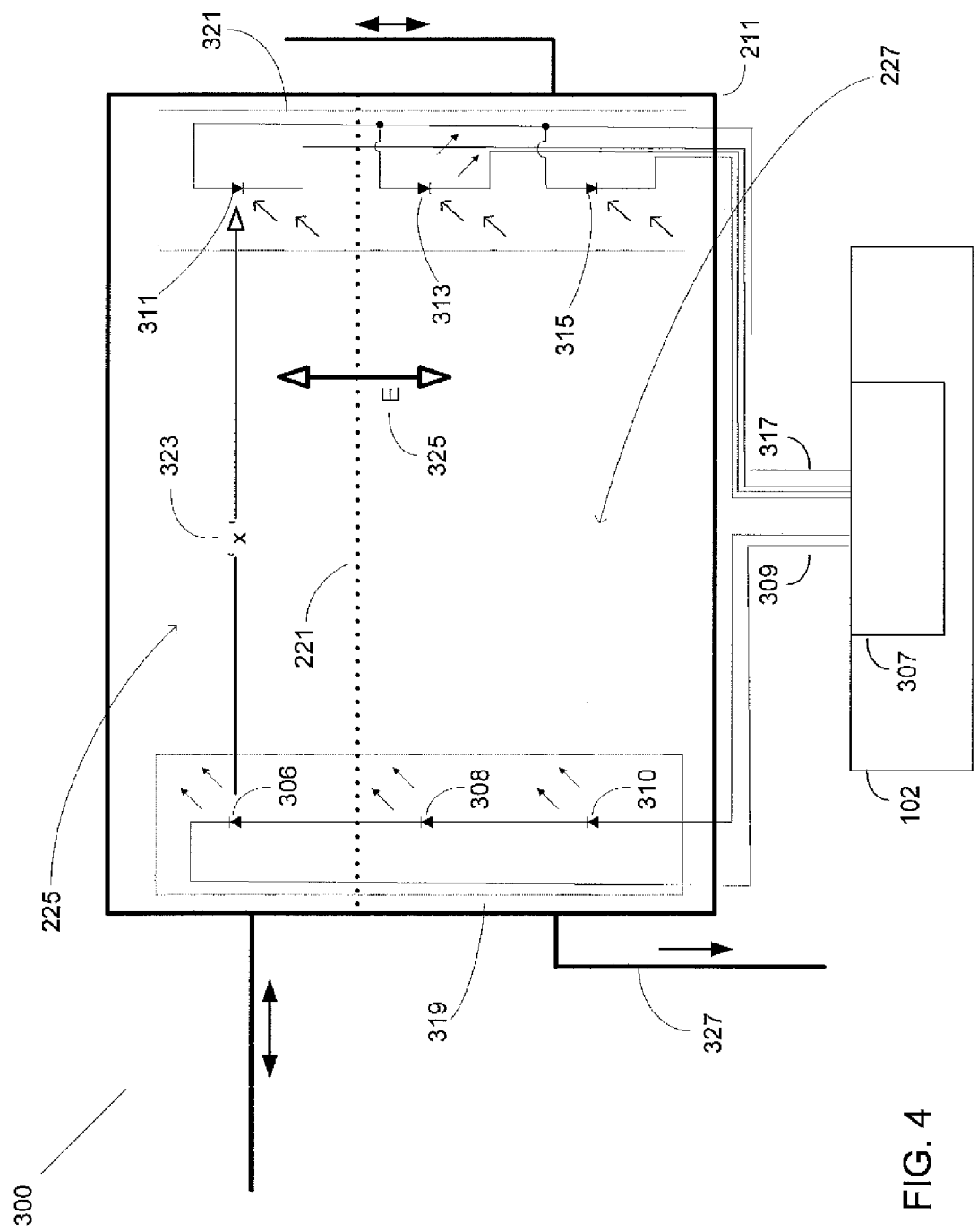
FIG. 4 illustrates an optical fluid level detection and sensing system for a surgical cassette reservoir including an electric circuit where three pairs of emitter-detector devices are configured to form three separate power output signals.
Figure 5:
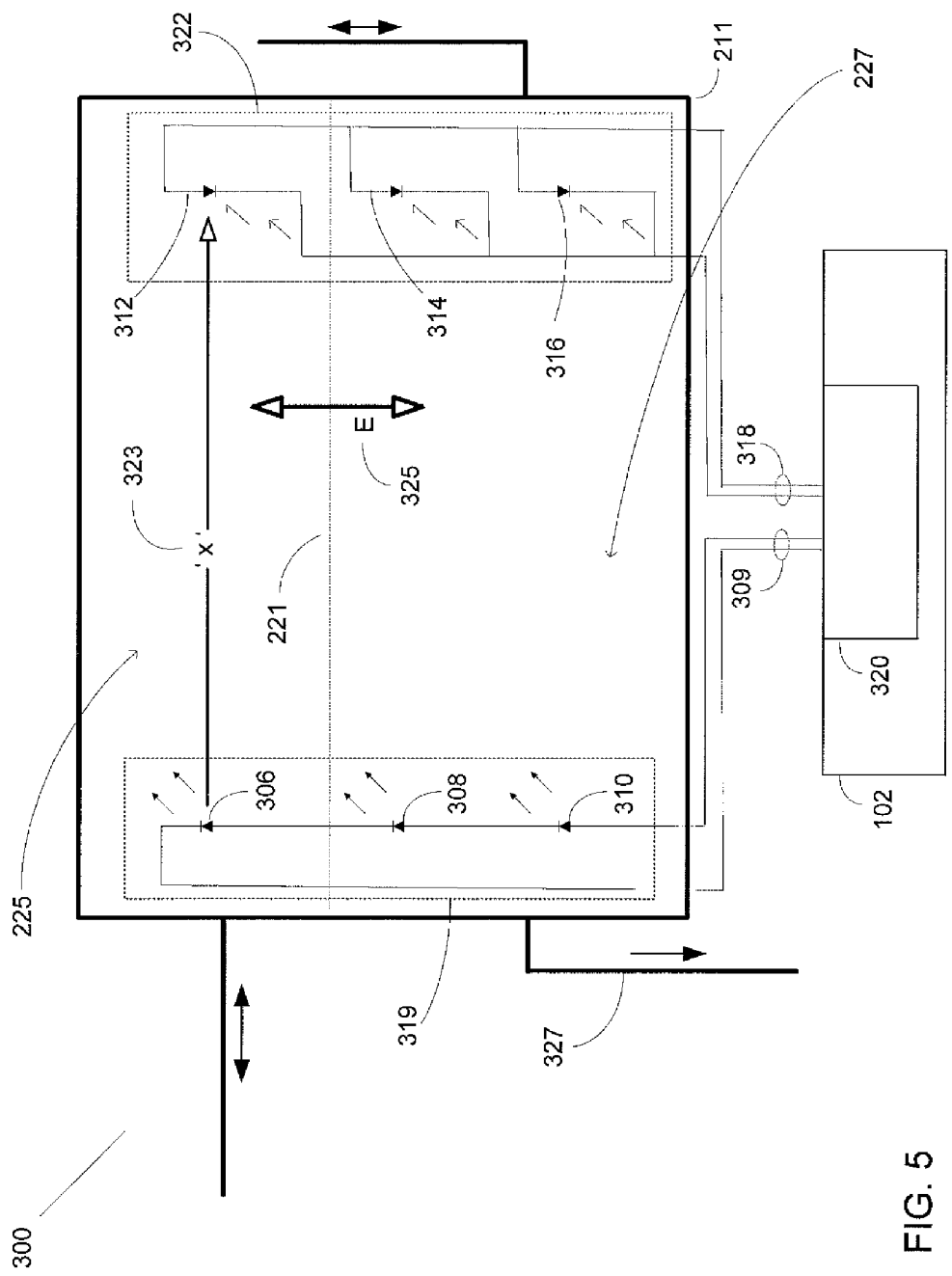
FIG. 5 illustrates an optical fluid level detection and sensing system for a surgical cassette reservoir including an electric circuit where three pairs of emitter-detector devices are configured to form a combined power output signal.

FIGS. 4 and 5 illustrate various exemplary embodiments for the present design's fluid level detection (FLD) system 300 involving multiple fluid level emitter-detector device pairs configured at different vertical heights within the reservoir. FIG. 4 shows where three pairs of emitter-detector devices are configured to form three distinct optical power output detection signals available for driving three separate detection circuits (not shown). FIG. 5 shows three pairs of emitter and detector devices configured to form a combined or summed power output signal.

In each of these illustrated arrangements, the present design may provide a plurality of emitter-detector device pairs arranged along the walls of the fluid detection chamber portion of the reservoir for determining fluid level in the reservoir. The present design may detect fluid level from multiple distinct vertical heights within the reservoir by arranging emitter-detector device pairs at a number of discrete points, such as at a high, middle, and a low position within the reservoir as shown in FIGS. 4 and 5.

For the embodiments shown in FIGS. 4 and 5, FLD system 300 may affix or attach a first, or highest positioned, emitter device 306, a mid level emitter device 308, and a third lower level positioned emitter device 310 attached to the inside of reservoir 211 within the cassette. Emitter devices 306, 308, and 310 may be electrically connected to electric circuit 307 at point 309 as shown in FIG. 4. Note that the three emitting diodes shown in FIG. 4 can be controlled individually for calibration purposes or other appropriate purposes. Driving the electric circuit in this manner may allow for transmitting optical wavelength energy through the reservoir at various predetermined heights.

FLD system 300, as shown in FIGS. 4 and 5, may detect the fluid level within reservoir 211 in relation to the amount of optical energy received from multiple detectors, which are paired horizontally across from the emitter device positions, where the present designs may locate the detector devices at positions 311, 313, and 315 in FIG. 4 and positions 312, 314, and 316 in FIG. 5. The present design may configure the detector devices at positions 311, 313, and 315 in an individual reporting arrangement as shown in FIG. 4 at point 317, or in a collective or combined reporting arrangement, as shown in FIG. 5 at point 318, where electric circuit 307 in FIG. 4 and electric circuit 320 in FIG. 5 may be configured to receive the total voltage amplitude from the sum of the three detectors.

In each embodiment, the present design may determine the total amount of energy realized from all three detectors sufficient to sense the fluid level inside reservoir 211.

FIG. 4 illustrates an FLD system 300 for reservoir 211 in a device such as cassette 201 as illustrated in FIGS. 2A and 2B. FIG. 4 illustrates an optical fluid level detection and control system for the cassette reservoir including an electric circuit where three pairs of emitter-detector devices are configured to form three separate power output signals. Electric circuit 307 may comprise emitter array 319, for example photodiodes, configured to transmit light energy across multiple transmission paths, such as high, middle, and low, through the reservoir. The present design may orient detector array 321 at the opposite end of the reservoir, configured to receive light energy from multiple distinct paths, in alignment with the emitting devices matching the high, middle, and low vertical height positions for the emitting devices within the reservoir. The emitter and detector device pairs may be provided in a parallel orientation as illustrated in FIGS. 4 and 5.

The emitter and detector device pairs may be part of the surgical cassette including the reservoir, for example located and fixed on the inside walls of the reservoir. Locating the emitter-detector device pairs inside the reservoir may require the present design to be electrically isolated from the fluid, such as by use of insulation or other isolating methodology known in the art.

It is specifically noted that the emitter and detector pairs may be located inside or outside the reservoir and may be attached to the outside of the reservoir or be a part of the instrument host. One implementation, as discussed, entails having the FLD in the instrument host because many of the cassettes are disposable.

In the embodiment illustrated in FIG. 4, FLD system 300 may include emitter array 319 and detector array 321 oriented in a paired configuration, and may attach to the inside of reservoir 211 within the cassette separated by a distance 'x' as shown at point 323. The present design emitter array 319 may electrically connect to electric circuit 307 at point 309 and detector array 321 may electrically connect to electric circuit 307 at point 317, as shown in FIG. 4. The connections may be realized using a pogo pin male type connector, or equivalent connector, configured to plug into a companion pogo pin female connector provided as part of instrument host 102 electric circuit 307.

Electric circuit 307 may include electrical components, such as passive devices such as resistors and active devices such as diodes connected to a power source, such as circuit for generating a voltage to drive the emitting devices, and a circuit for receiving a signal from each of the detecting devices. Operating the electric circuit in this manner may allow for determining the amount of optical energy received by the detecting devices after traveling through the contents of the reservoir by the emitter-detector array pair arrangement inside reservoir 211.

FLD system 300 may detect and determine the fluid level within reservoir 211 in relation to the amount of optical energy received from each detecting device, within detector array 321.

The present design may configure electric circuit 307 to determine the output signal produced from each detecting device. For example, the present design may involve three identical detection circuits, where each circuit is connected to a corresponding detecting device, where one detecting device is located or positioned high in the reservoir, a second detecting device located at the middle of the reservoir, and a third detection device located at a low point or near the bottom of the reservoir.

In the situation where the reservoir is nearing an empty state during an optical procedure and the reservoir primarily contains air, each detecting circuit may receive a signal representing received un-attenuated optical or light energy. A simple sample and hold circuit may be used with each detecting device, where the sample and hold circuit may produce an output signal representing a 'ON' state or in digital logic terms a '1' when the optical energy received from the detector is greater than a predetermined value. For this example, if the electrical circuit 307 determines all three detection circuit levels are at the 'ON' state, the system determines that no appreciable optical signal attenuation exists, indicating an empty or near empty condition. The present design may start a peristaltic pump or other device to add fluid to the reservoir, from a BSS infusion bottle for example.

As the reservoir begins to fill, the lowest detector device in detector array 321 may report a reduction in optical signal intensity, due to the attenuation resulting from the signal now passing through the fluid, as the optical path of the lowest positioned detector becomes submerged in fluid. This attenuated signal can be detected as a change to an 'OFF' state or logic level '0'. With a fluid level above the lowest detector device and below the middle detector device, the present design may determine additional fluid is no longer required. As the surgical procedure progresses, the reservoir may become filled primarily with fluid, aspirated from the patient's eye. As this fluid level rises, the optical path of the middle detector device may become submerged in fluid. At this point, the detector device output signal may fall below the preset value causing both the lower and middle detector devices to report an 'OFF' state or a logic level '0'. To prevent an over-filled condition, the fluid in the reservoir will begin to drain from the reservoir to the collection bag.

As the surgical procedure continues, it may be possible for the fluid level to continue to rise. In the case where the fluid level continues to rise above the optical path of the highest detector device, the instrument host may pause the aspiration of fluid from the patient's eye while still continuing using a peristaltic pump or other appropriate device or procedure to remove fluid from the reservoir. This pause allows the fluid level within the reservoir to return to a safe operational level.

Conversely, as the fluid level within the reservoir begins to decrease the middle and highest detector device will report an increase in the optical signal intensity, due to the fluid no longer attenuating the signal. This signal increase causes the detector device to change to an 'ON' state or logic level '1' as the fluid level decreases to below the optical path of each respective detector device.

Table 1 summarizes this representative example by providing for detector output signal states versus fluid level and the present design's control actions.

TABLE 1

Fluid Level Versus Detector Output Signal

| | DETECTOR DEVICE STATE | | | |
|---|---|---|---|---|
| FLUID LEVEL | High Sensor | Middle Sensor | Low Sensor | CONTROL ACTION |
| High | OFF | OFF | OFF | Pause Aspiration and continue to Drain |
| Mid | ON | OFF | OFF | Drain |
| Low | ON | ON | OFF | Hold/Fill |
| Empty | ON | ON | ON | Fill |

The FLD system 300 may determine the output signal resulting from a plurality of emitter-detector device pairs using electric circuit 307 and communicate a signal, such as a voltage reading or digital signal, indicating an increase or decrease in fluid level to instrument host 102 as a result of an increase or decrease in fluid shown by arrow E 325. In this "stepped" configuration, where the fluid level has fallen below the set of detector devices in detector array 321, FLD system 300 may measure the voltage amplitude realized from each detector device using electric circuit 307 and communicate a signal indicating an increase or decrease in each measured voltage amplitude at each measurement height to instrument host 102 as a result of an increase or decrease in fluid shown by arrow E 325. Air in section 225 and fluid in section 227 are separated by air-fluid interface 221.

FLD system 300 may involve one or more photocurrent amplifiers to generate the disclosed voltage response, from for example a photocurrent-to-voltage conversion circuit (not shown) and may configure the output from each detector device as multiple individual responses from detector array 321 or a summed response from detector array 322 shown in FIG. 5.

The present design may individually detect voltage at each detection device, using individual measuring circuits, for indicating when fluid has reached and covered or submerged the detector device(s). Instrument host 102 may control a pump to operate and move fluid from the reservoir to the collection bag or other collecting device based on a decrease in received signals using flexible surgical tubing 327.

For example, if all three detector devices report a low voltage amplitude value to instrument host 102, the host may determine that the fluid level is high and may control the peristaltic reservoir pump to operate and move fluid from the reservoir to the collection bag.

Similarly, the instrument host 102 may control a pump or other appropriate device to operate and move fluid from a fluid source such as a BSS infusion bottle to the reservoir based on a communicated increase in output signals. Instrument host 102 may control a pump, such as a peristaltic reservoir pump or an additional pump, to operate and move fluid from a source, such as a BSS infusion bottle to reservoir 211 based on signals, such as voltage readings, from detector devices positioned at each height. For example, if all three detector devices report a high voltage amplitude value to instrument host 102, the host may determine that the fluid level is low and either add fluid to the reservoir from a source, or continue to employ aspiration to increase fluid in the reservoir, in either case continuing to monitor the fluid level. Conversely, if all three detector devices report a low voltage amplitude value to instrument host 102, the host may determine that the fluid level is high and drain fluid from the reservoir, such as by a pump moving excess fluid from the reservoir and into a collection bag.

It is to be understood that any number of detectors may be used and coverage of any number of detectors by fluid may represent the middle, low, and or high points of the fluid, and different orientations and configurations may be employed using the devices and teachings herein.

FIG. 5 illustrates an alternate embodiment for an FLD system 300 where the cassette reservoir may include an electric circuit arrangement where the output signals from three detector device pairs are summed to form a single combined power output signal.

FIG. 5 illustrates FLD system 300 including reservoir 211 in a device such as cassette 201 as illustrated in FIGS. 2A and 2B in accordance with a further embodiment of the present design. FIG. 5 illustrates an optical fluid level detection and control system for a surgical cassette reservoir including an electric circuit where separate detector devices may be positioned at differing heights within reservoir 211 as illustrated in FIG. 5. The present design may form a single output signal representing the output of parallel-connected detector array 322. Electric circuit 308 comprises emitter array 319, for example photo-diodes, configured to transmit light energy across multiple horizontal paths, such as at high, middle, and low, through the reservoir. The present design may arrange detector array 322 at the opposite end of the reservoir from emitter array 319, configured to receive light energy from multiple distinct paths, and in horizontal alignment with the emitting devices, and in this example matching the high, middle, and low positions for the emitting devices, through the reservoir. The present design may orient the emitter and detector arrays in this parallel orientation or in horizontal alignment with respect to each other as illustrated in FIG. 5.

In the embodiment illustrated in FIG. 5, FLD system 300 may include emitter array 319 and parallel-connected detector array 322 oriented in a paired configuration, and may attached to the inside of reservoir 211 within the cassette separated by a distance 'x' as shown at point 323. The present design emitter array 319 may be electrically connected to electric circuit 320 at point 309 and detector array 322 may be electrically connected to electric circuit 308 at point 318, as shown in FIG. 5.

Electric circuit 308 may include electrical components, such as passive devices such as resistors and active devices such as diodes connected to a power source, such as circuit for generating a voltage to drive the emitting devices. Electric circuit 320 may also or alternately include a circuit for receiving a signal from the sum of the detecting devices, configured in parallel. Operating the electric circuit in this manner may determine the amount of optical energy received by all the detecting devices after traveling through the contents of the reservoir by the emitter-detector array pair arrangement inside reservoir 211.

FLD system 300 may detect and determine the fluid level within reservoir 211 in relation to the amount of total optical energy received from all detecting devices, realized across detector devices 312, 314 and 316 as shown in FIG. 5 and summed by electric circuit 320.

The present design may configure electric circuit 308 to determine the output signal produced from combining all three detecting devices. For example, the present design may involve a single detection circuit, where the detection circuit is configured to receive the total energy produced from the three detecting devices, where one detecting device is located or positioned high in the reservoir, a second detecting device located at the middle of the reservoir, and a third detection device located at a low point or near the bottom of the reservoir.

In the situation where the reservoir is near empty during an optical procedure, where the reservoir contents are primarily air, the detecting circuit may receive a signal representing an amount of received un-attenuated optical energy equal to the sum of the full output for all three detector devices. A simple sample and hold circuit may be used with the detecting devices where the sample and hold circuit may produce an output signal representing a 'first' state when the optical energy received from the sum of detectors is at a value greater than a predetermined value established for representing a near empty reservoir or tank condition. For this example, if electrical circuit 308 determines the detection circuit output signal levels are at the 'first' state, the system may determine that there is no appreciable optical signal attenuation, after following multiple transmission paths through the reservoir for each detector level, resulting from the absence of fluid.

As the reservoir begins to fill, the lowest detector device may report a decrease in signal intensity, due to the increased attenuation resulting from the signal passing through the fluid, where the lowest detector device is now submerged in fluid. As the reservoir continues to be filled by the pump, the middle detector may become submerged in fluid. At this point, the electric circuit output signal may decrease below a preset value causing the detecting circuit to report a 'middle' level condition. If the instrument host determines that the reservoir has been replenished sufficient to maintain the desired air to fluid ratio, the present design may be configured to stop the pump.

Conversely, as the optical procedure progresses, the reservoir may become filled primarily with fluid and ocular material, aspirated from the patients eye, where the reservoir needs to be drained by moving fluid from the reservoir to the collection bag. In the situation where all three detecting devices are submerged in fluid, the detecting circuit may be configured to report a reduced or attenuated output signal where all three detection device levels are at a 'low' state. When the instrument host receives a 'low' state condition from electric circuit 308, the present design may start a pump, such as a peristaltic pump, to remove fluid from the reservoir. As the pump operates, the fluid level within the reservoir may go down. When the fluid level drops below the high level and middle level detectors, causing them to toggle from their present 'low' output state to the 'high' state as the optical transmission paths contains only air, the present design may stop the pump.

FIGS. 6 and 7 provide left and right views (top, side, and front views) of an embodiment of the present cassette arrangement where photo-diodes are fixed with, as an integral or integrated part in, a device such as cassette 201 as disclosed previously in FIGS. 2A and 2B. In the case of where the light source and the light sensor are attached to the reservoir, they may be inside or outside the reservoir. Preference may be outside to prevent a direct connection through conductive fluid to the electronics. If inside, the light source and light sensor are electrically isolated from the fluid, such as by use of insulation, hermetically sealed, or other isolating methodology known in the art.

The present design's left side is shown in FIG. 6 and illustrates transparent window 351 where three emitting photo-diodes 353 are mounted or packaged, for example hermetically sealed, with transparent window 351. Top view 377 and side view 378 are presented. Connector 355 may enable the emitting devices to be electrically attached to the instrument host. The present design's right side is shown in FIG. 7 and illustrates transparent window 357 with three detecting photo-diodes 359 are mounted or packaged with transparent window 357. Top view 395 and side view 396 are also shown. Connector 361 may enable the detecting devices within cassette 201 to electrically attach and form an electric circuit with the instrument host.

The emitting and detecting devices may be configured as arrays and may be part of the instrument into which the cassette including the reservoir is inserted. Emitting and detecting arrays may therefore be positioned outside of the reservoir and outside of the cassette, on the instrument into which the cassette is mounted. An example of this type of mounting or operation is provided in FIG. 10.

FIGS. 8 and 9 provide left side and right side views (front, top, and side views) for an embodiment of the cassette 201 arrangement where emitting and detecting photo-diodes are physically located separate from the cassette. In this configuration, the present design may fix or locate the emitting and detecting photodiodes outside of the surgical cassette where the photodiodes are attached and mounted with the instrument host.

FIG. 8 illustrates the present design's cassette left side where a window 363 is located on an outside wall of cassette 201. The present design may locate the emitting photo-diodes outside of window 363 configured to provide a light source for transmission through the reservoir. Top view 385 and side view 386 are illustrated. FIG. 9 illustrates the present design's cassette right side where window 365 is located on the outside wall of cassette 201 opposite and opposing to window 363. The present design may locate the detecting photo-diodes outside of window 365 configured to provide a light sensor for reception of energy transmitted from the light source through the reservoir. Top view 397 and side view 398 are also shown.

When cassette 201 is loaded into instrument host 102, as shown in FIG. 10, window 363 may enable emitter array 367 to transmit light waves at 369*a*, 369*b*, and 369*c* into reservoir 211. Window 365 may enable detector array 371 to receive light exiting from reservoir 211 through window 365. FIG. 10 provides a centerline split perspective view illustrating a combined left and right side views for cassette 201 loaded into holder (or cassette receptacle) 375 where holder 375 is part of instrument host 102. The left side from centerline 373 illustrates emitter array 367 integrated with instrument host 102 and transmitting optical waves 369*a*, 369*b*, and 369*c* through window 363 and exiting from window 365 towards detector array 371. The cassette in FIG. 10 may be inserted and removed from the instrument host holder 375.

Figure 11:
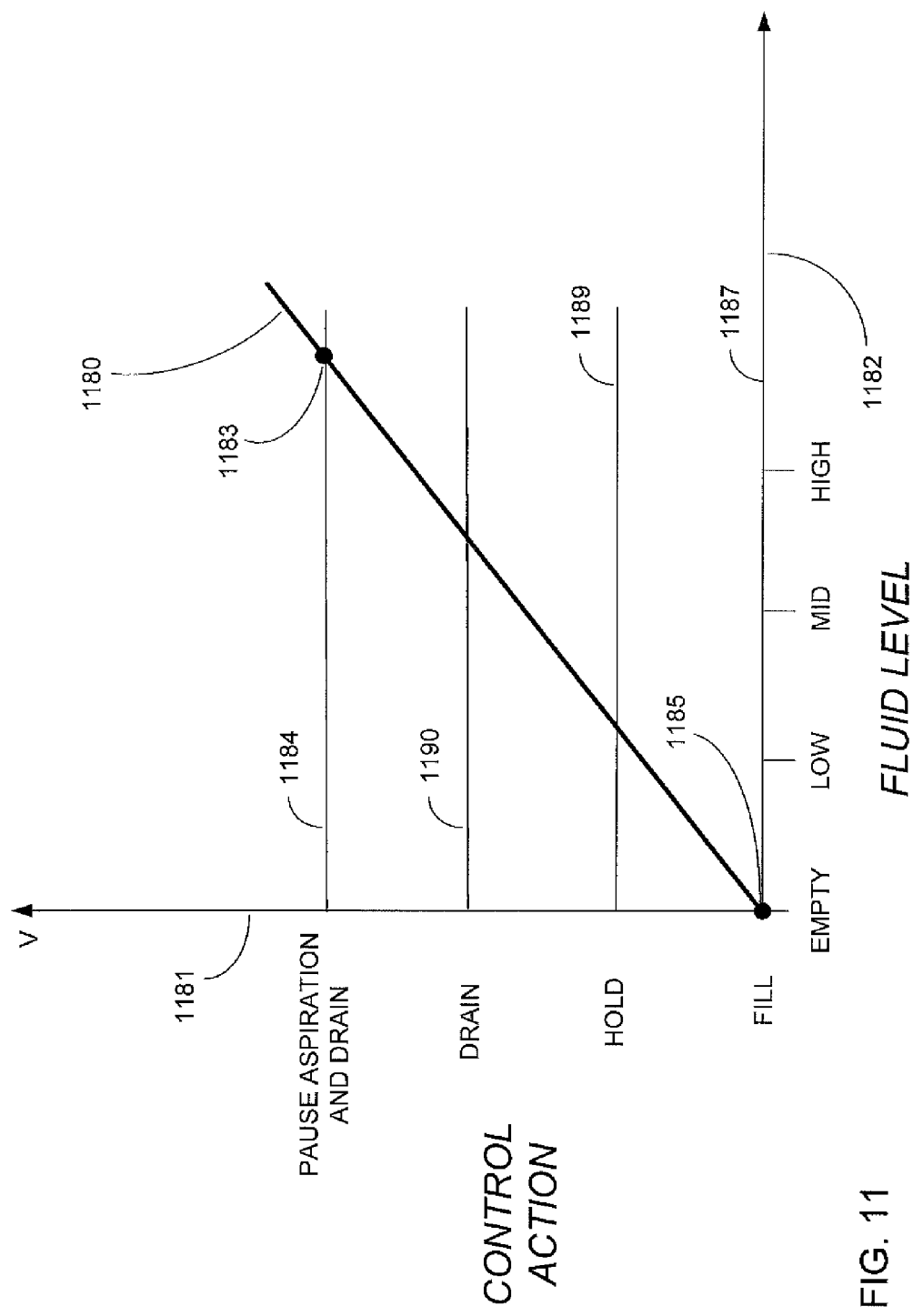
FIG. 11 illustrates a general approximation for a linear graph representing the sum of three detector output signal levels and desired control action versus reservoir fluid level and the present design's control actions.

FIG. 11 illustrates an approximate linear graph 1180 representing the sum of the detector device output signal levels and desired control action versus reservoir fluid level. The response is plotted as voltage (on axis 1181) versus reservoir fluid level (on axis 1182). The response curve illustrates the voltage measured and summed from three detector devices submerged by fluid is shown at 1183 and the voltage measured and summed for all three detector devices exposed to air is shown as response 1185.

FIG. 11 illustrates three preset voltage values and relates these values to instrument host control circuit actions. For example, the preset voltage value 1187 indicates a near zero (or below a threshold value) output is measured from electric circuit 1108 wherein the optical paths of all detector devices are transmitted through air indicating the reservoir needs to be filled. The voltage value 389 indicates approximately one third of the total output is measured from electric circuit 1108 wherein the optical path of the middle and top detector devices are exposed to air while the optical path of the low detector device is submerged by fluid indicating an acceptable balance of fluid and air within the reservoir. The voltage value 1190 indicates two thirds of the total output is measured from electric circuit 1108 wherein the optical path of the top detector device is exposed to air while the optical path of the middle and lowest positioned detector devices remain submerged by fluid indicating the reservoir needs to be drained to maintain a balanced air to fluid ratio within the reservoir. The voltage value 1184 indicates the optical paths of all detector devices are submerged indicating the fluid being aspirated into the reservoir is surpassing the amount of fluid being drained from the reservoir. The instrument host 102 can limit the amount of fluid being aspirated into the reservoir 201 by pausing the aspiration function to allow the fluid level to return to the desired operational range.

FIG. 12 illustrates an exemplary optical fluid level detection system that may involve multiple optical detector devices to realize level detection at multiple vertical heights within reservoir 211 and may connect the optical detector device array 1291 to summation converter 1293. Summation converter 1293 may vary the voltage response output signal 1295 in response to the optical power signal level measured at summation converter 1293. Fluid level control circuit 1297 may receive voltage response output signal 1295 and based on this signal may operate pump 209 by turning it on or off using control signal 1299. When control circuit 1297 processes signal 1295 and turns on pump 209, fluid is removed from reservoir 211 and moved to collection bag 205 as previously described.

Additional circuits may include, but are not limited to, varying output voltage, current, pulse width, duty cycle, or digital representation in response to changes in individual or total optical power received.

Although three emitter devices are represented in an array and three detector or sensor devices are also shown in an array in FIG. 4 and FIG. 5 at specific physical locations within the reservoir, the present design is not limited to using three device pairs nor an array configuration and may be realized using additional device pairs at other locations within the reservoir. Furthermore, an additional device pair may be located at the top or high level within the reservoir and configured to operate as a backup or redundant detecting device. The illustrations that form FIGS. 4 and 5 are generally not drawn to scale and are for illustrative purposes.

Figure 13:
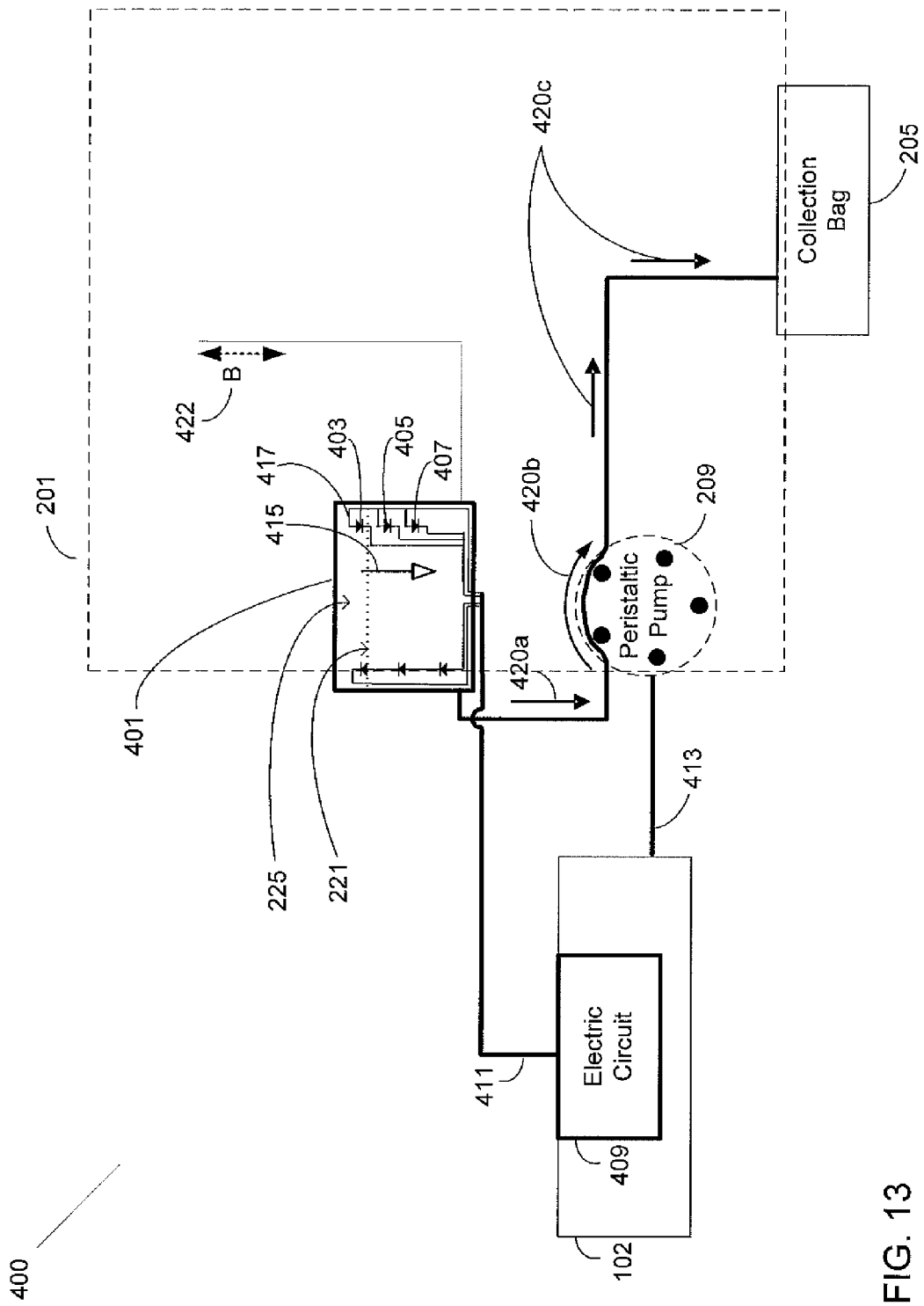
FIG. 13 is a functional block diagram illustrating a surgical cassette system configured for peristaltic pump outflow operation.

FIG. 13 illustrates a mode of operation for the present design. FLD system 400 with cassette 201 may employ peristaltic pump 209 to move fluid from reservoir 401 to collection bag 205 as a result of a high level of fluid in reservoir 401. In this arrangement, detector device 403, 405, and 407 all may report a low output signal level to electric circuit 409 via a connection 411 due to fluid covering the three detectors. Electric circuit 409 may convert the reported signal levels into a voltage response or digital representation sufficient to indicate to instrument host 102 to operate peristaltic pump 209 via connection 413 to pump fluid from reservoir 401 to collector or collection bag 205.

As instrument host 102 runs pump 209, the amount of fluid decreases as indicated by arrow 415. As the fluid decreases and detector array 417 is exposed to air in air space 225, the voltage response or digital representation reported to instrument host 102 increases. As the fluid level drains below detector device 405, the reported voltage response further increases. When air-fluid boundary 221 is reduced below detector device 407, the reported voltage response may rise above a certain threshold indicating reservoir 401 is drained and the instrument host may stop pump 209. Operating pump 209 may move fluid from reservoir 401 to collector or collection bag 205 along the path indicated by arrows 420*a, b*, and *c*. General fluid flow to other parts of the design is shown as arrow B 422.

Figure 14:
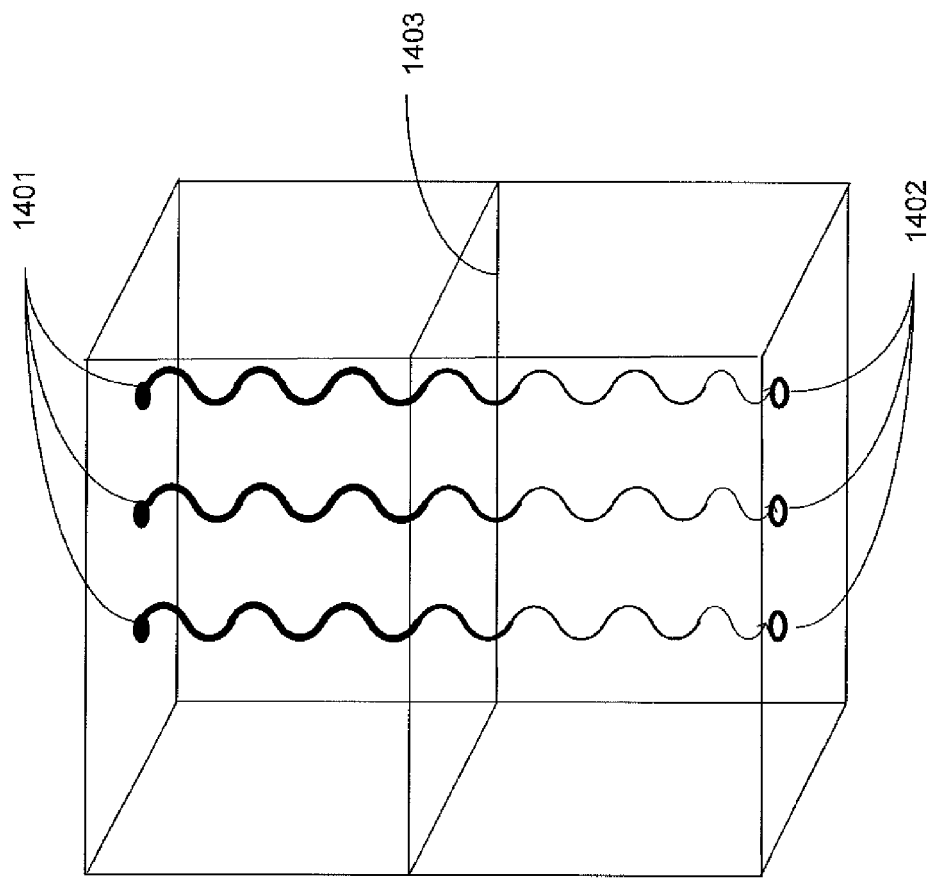
FIG. 14 illustrates an alternate embodiment of determining the fluid level using an analog measurement with predetermined voltage level thresholds for controlling the required fill/hold/drain actions.

The present design may orient the individual emitter devices or the emitter array in a vertical orientation with respect to detector devices or detector array as illustrated in FIGS. 6, 7, 8, and 9. FIG. 14 illustrates an alternate mode of determining the fluid level using an analog measurement with predetermined voltage level thresholds for controlling the required fill/hold/drain actions. Emitters 1401 are illustrated, and again, any number of emitters may be employed. Three emitters 1401 are shown in FIG. 14. Detectors 1402 are illustrated, and fluid level 1403 is provided. In this configuration, the emitters 1401 and detectors 1403 are positioned at the top and bottom of the reservoir and take an analog measurement of the fluid level rather than at discrete levels. Optical attenuation is based on the absorption calculations provided above.

A vertical orientation allows multiple control actions to be determined using a single emitter/detector pair, although more than one emitter/detector pair may be employed. This configuration provides better resolution of the fluid level measurement, while minimizing the amount of required detector devices.

In sum, the present design of an optical fluid level detection system provides for automatic draining or filling of fluid within the reservoir during an ocular procedure by operating a pump, for example a vacuum, venturi, or peristaltic pump, using optical detection for level sensing. The present design does not require a fluid float mechanism and thus is free of incorrect measurements due to a stuck or "sunk" float condition.

The presence of BSS beads and condensation on the sides of the reservoir tank has previously made reflected and refracted level detection difficult. The present design can offer beneficial performance as compared with such previous designs. Residue in the form of beads and condensation in an "empty" or "low" condition, where fluid is drained from the reservoir but a residue has built around either the transmitter or sensor, merely results in a slightly lower light energy reading rather than a completely improper reading. As noted, if a predetermined energy level sets the difference between a full and empty condition, the presence of residue or BSS beads in the presence of light energy transmitted as disclosed herein yields a reading still above the predetermined energy level, indicating an empty condition. Devices that work on the basis of refraction cannot offer such performance—even minor residue on the transmitter or receiver can result in reading errors.

Thus in general, automatic or semi-automatic operation entails sensing a drop or rise in a voltage or digital response and either drains fluid from the reservoir or pumps fluid into the reservoir. In any circumstance, the surgeon or other personnel is provided with the ability to run the pumps in any available direction, such as for cleaning purposes.

The desire is to maintain hygienic conditions and fluids in the components shown. Periodic cleaning of the reservoir may occur using peristaltic pump 205 and the reservoir may be refilled. Other pumping states may be provided as discussed herein and may be employed based on the desires of personnel performing the surgical procedure. Other configurations may be provided, including limiting the voltage response of the electric circuit, thus the detector device output signal level, optical fluid level detecting device to be within a desired range, and so forth.

The terms transmitter and emitter as used herein are interchangeable and the terms receiver and detector as used herein are also interchangeable.

The design presented herein and the specific aspects illustrated are meant not to be limiting, but may include alternate components while still incorporating the teachings and benefits of the invention. While the invention has thus been described in connection with specific embodiments thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains.

The foregoing description of specific embodiments reveals the general nature of the disclosure sufficiently that others can, by applying current knowledge, readily modify and/or adapt the system and method for various applications without departing from the general concept. Therefore, such adaptations and modifications are within the meaning and range of equivalents of the disclosed embodiments. The phraseology or terminology employed herein is for the purpose of description and not of limitation.

What is claimed is:

1. A medical device, comprising:
a plurality of transmitters and a numerically matching plurality of receivers forming transmitter-receiver pairs positioned in association with a fluid maintaining device associated with the medical device;
circuitry configured to drive the transmitter to transmit light energy to said fluid maintaining device; and
a controller configured to receive data from the receiver and determine fluid level in said fluid maintaining device;
wherein each transmitter of the plurality of transmitters is configured to transmit light energy at a predetermined wavelength forming a signal distinct from the other of the plurality of transmitters, each receiver of the plurality of receivers continuously receives light energy from the paired transmitter when the paired transmitter transmits light energy, and the controller is further configured to determine presence and absence of fluid in said fluid maintaining device based on an amount of light energy received at each receiver of the plurality of receivers;
wherein the amount of light energy received at each receiver of the plurality of receivers is based on the predetermined wavelength of the light energy, a distance between the transmitter and the receiver of the transmitter-receiver pair, and an absorption coefficient for fluid expected to be employed in the fluid maintaining device, such that light energy below a predetermined nonzero value received at a receiver of the plurality of receivers indicates fluid presence at the receiver level in the fluid maintaining device and light energy above the predetermined nonzero value received at a receiver of the plurality of receivers indicates an absence of fluid at the receiver level in the fluid maintaining device.

2. The medical device of claim 1, wherein each receiver of the plurality of receivers is at a substantially same height as the paired transmitter and receives light energy when transmitted in the presence of fluid and in the absence of fluid.

3. The medical device of claim 2, wherein the presence of an excess amount of fluid in the fluid maintaining device determined by the controller causes the controller to provide an indication to expel fluid from the fluid maintaining device.

4. The medical device of claim 1, wherein the receiver of each of the plurality of transmitter-receiver pairs is configured to receive light energy transmitted through the fluid maintaining device originating from said paired transmitter.

5. The medical device of claim 1, wherein fluid may be added to the fluid maintaining device based on an amount of fluid present in the fluid maintaining device as determined by the controller.

6. The medical device of claim 1, wherein the transmitter and receiver of a transmitter-receiver pair are positioned external to the fluid maintaining device.

7. The medical device of claim 1, wherein the transmitter and receiver of a transmitter-receiver pair are positioned within the fluid maintaining device.

8. The medical device of claim 1, wherein the transmitter and receiver of a transmitter-receiver pair are positioned vertically with respect to the fluid maintaining device.

9. The medical device of claim 1, wherein the predetermined wavelength is between approximately 950 nm and 1550 nm.

10. The medical device of claim 1, wherein each transmitter of the plurality of transmitters comprises a transmitter array and each receiver of the plurality of receivers comprises a receiver array.

11. A method of controlling a fluid level in a fluid maintaining device, comprising:
emitting light from one or more of a plurality of transmitters at a predetermined wavelength forming a signal distinct from the other of the plurality of transmitters positioned in association with the fluid maintaining device through said fluid maintaining device;
sensing the light from the fluid maintaining device continuously at one or more of a numerically matching plurality of receivers positioned in association with the fluid maintaining device, wherein said sensing comprises the one or more receivers continuously receiving light energy from the fluid maintaining device when the one or more transmitters is/are transmitting light energy; and adjusting the fluid level in the fluid maintaining device based on sensed light and an absorption coefficient for the type of fluid expected to be employed in the fluid maintaining device;

wherein a quantity of light energy sensed by a receiver of the plurality of receivers below a nonzero threshold constitutes the presence of fluid at the level of that receiver, the nonzero threshold based on a wavelength of light transmitted, distance between the transmitter and receiver, type of fluid expected to be employed in the fluid maintaining device and the absorption coefficient, and further wherein the quantity of light energy sensed by each receiver in excess of the nonzero threshold constitutes an absence of fluid at the level of each receiver.

12. The method of claim 11, wherein adjusting the fluid level comprises activating a pump to increase or decrease the fluid level in the fluid maintaining device.

13. The method of claim 11, wherein the emitted light from each of the plurality of transmitters has a wavelength between approximately 950 nm and approximately 1550 nm.

14. The method of claim 11, wherein the fluid maintaining device is a component of an ophthalmic surgical device.

15. A medical device, comprising:
a transmitter array comprising a plurality of light energy transmitters positioned in association with a fluid maintaining device;
electrical circuitry connected to the transmitter array and configured to cause the transmitter array to transmit light energy at a predetermined wavelength forming a signal distinct from the other of the plurality of transmitters;
a receiver array comprising a numerically matching plurality of receivers, each of the plurality of receivers paired with one of the plurality of transmitters continuously receiving light energy transmitted through the fluid maintaining device and originating from the paired transmitter of the transmitter array when the transmitter array is transmitting light energy; and
a controller configured to determine fluid level in the fluid maintaining device based on conditions sensed by the receiver array such that conditions below a nonzero threshold constitute the presence of fluid in the fluid maintaining device at a level of the receiver array and conditions sensed by the receiver above the nonzero threshold constitute the absence of fluid in the fluid maintaining device at the level of the receiver array, the nonzero threshold based on the predetermined wavelength of the light energy, a distance between each transmitter-receiver pair of the transmitter array and the receiver array, and an absorption coefficient for fluid expected to be employed in the fluid maintaining device.

16. The medical device of claim 15, wherein the presence of an excess amount of fluid in the fluid maintaining device determined by the controller causes the controller to provide an indication to expel fluid from the fluid maintaining device.

17. The medical device of claim 15, wherein each of the plurality of light energy transmitters is placed at different desired locations in association with the fluid maintaining device and each of the plurality of sensors is positionally cooperating with the plurality of light energy transmitters.

18. The medical device of claim 15, wherein fluid may be added to the fluid maintaining device based on an amount of fluid present in the fluid maintaining device as determined by the controller.

19. The medical device of claim 15, wherein the receiver and transmitter arrays are positioned external to the fluid maintaining device.

20. The medical device of claim 15, wherein the receiver and transmitter arrays are positioned within the fluid maintaining device.

21. The medical device of claim 15, wherein the medical device is an ophthalmic surgical device.

\* \* \* \* \*